United States Patent
Conrad

(10) Patent No.: US 10,247,431 B2
(45) Date of Patent: Apr. 2, 2019

(54) FAN COIL APPARATUS INCLUDING A HUMIDIFICATION UNIT AND A HUMIDIFICATION UNIT

(71) Applicant: Omachron Intellectual Property Inc., Hampton (CA)

(72) Inventor: Wayne Ernest Conrad, Hampton (CA)

(73) Assignee: Omachron Intellectual Property Inc., Hampton, Ontario (CA)

(*) Notice: Subject to any disclaimer, the term of this patent is extended or adjusted under 35 U.S.C. 154(b) by 122 days.

(21) Appl. No.: 15/382,350

(22) Filed: Dec. 16, 2016

(65) Prior Publication Data

US 2018/0172291 A1 Jun. 21, 2018

(51) Int. Cl.
| F24F 3/00 | (2006.01) |
| B01F 3/04 | (2006.01) |
| F24F 3/16 | (2006.01) |
| F24F 1/0007 | (2019.01) |
| A61L 9/20 | (2006.01) |
| A61L 9/12 | (2006.01) |
| F24F 3/14 | (2006.01) |
| F24F 6/12 | (2006.01) |
| F24F 1/00 | (2019.01) |

(52) U.S. Cl.
CPC .............. F24F 3/16 (2013.01); A61L 9/122 (2013.01); A61L 9/20 (2013.01); B01F 3/04007 (2013.01); F24F 1/0007 (2013.01); F24F 3/14 (2013.01); F24F 6/12 (2013.01); A61L 2209/13 (2013.01); A61L 2209/211 (2013.01); A61L 2209/212 (2013.01); F24F 2001/0088 (2013.01); F24F 2003/1435 (2013.01); F24F 2003/1667 (2013.01); F24F 2003/1671 (2013.01); F24F 2003/1675 (2013.01)

(58) Field of Classification Search
CPC ............ F24F 3/14; B01F 3/04; B01F 3/04007
USPC ........................................ 96/223, 224, 226
See application file for complete search history.

(56) References Cited

U.S. PATENT DOCUMENTS

| 2,256,374 A * | 9/1941 | Cummings, Jr. ......... F24F 3/14 261/21 |
| 2010/0012291 A1* | 1/2010 | Sporie ................... F24F 5/0035 165/61 |

FOREIGN PATENT DOCUMENTS

| CA | 2746405 C | 10/2015 |
| CN | 204063306 U * | 12/2014 ................ F24F 6/12 |

* cited by examiner

*Primary Examiner* — Robert A Hopkins
(74) *Attorney, Agent, or Firm* — Philip C. Mendes da Costa; Bereskin & Parr LLP, S.E.N.C.R.L., s.r.l.

(57) ABSTRACT

A fan coil apparatus includes an air flow path, a humidification unit, and a treatment applicator. The air flow path extends from a heating zone to a fan coil air outlet, and includes a humidification section. The humidification unit includes a humidification unit water droplet outlet and an air permeable water retaining member. The air permeable water retaining member and the humidification unit water droplet outlet are provided in the humidification section and the air permeable water retaining member is positioned downstream from the humidification unit water droplet outlet. The treatment applicator provides a disinfecting agent upstream from an air outlet of the humidification section.

**12 Claims, 32

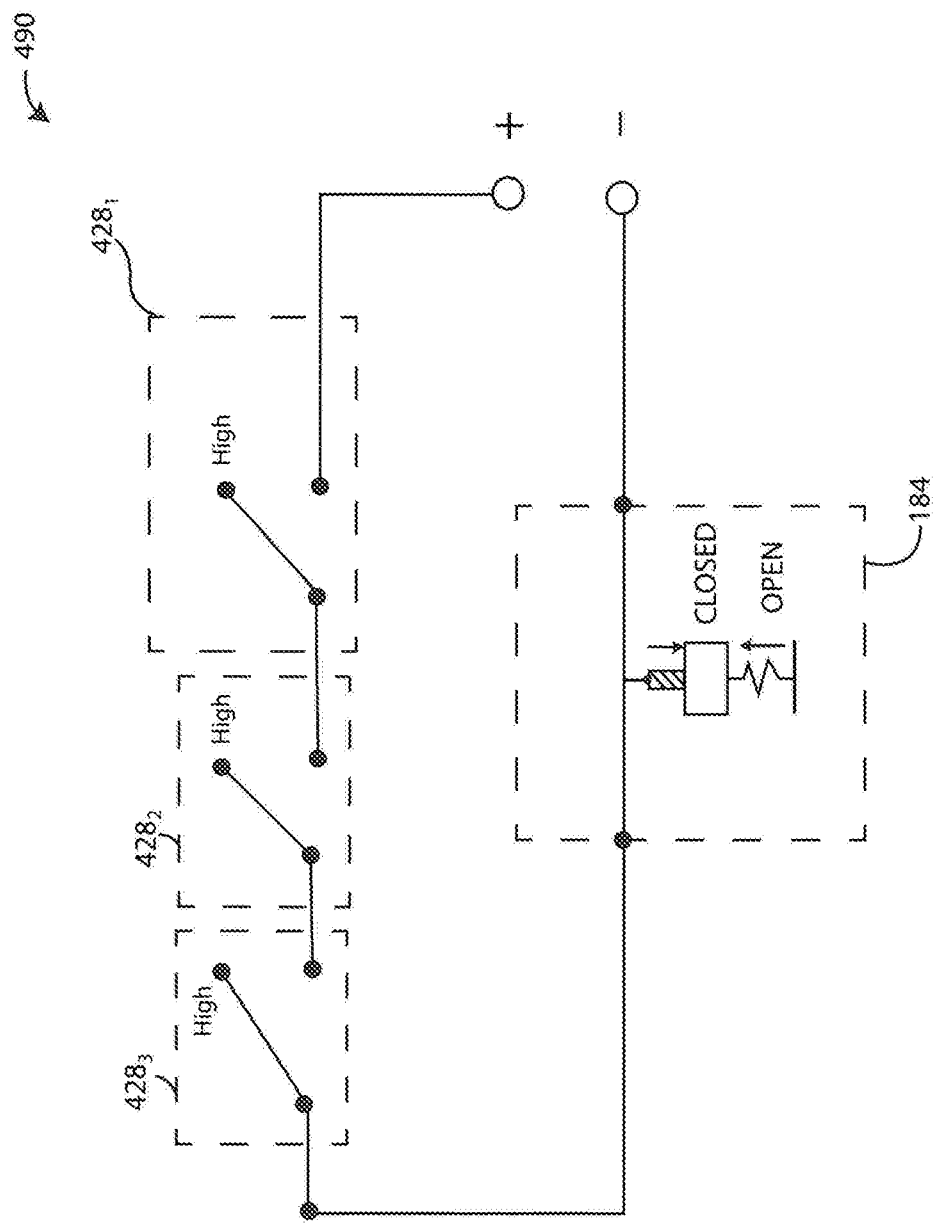

FAN COIL APPARATUS INCLUDING A HUMIDIFICATION UNIT AND A HUMIDIFICATION UNIT

FIELD

This application relates to fan coil apparatus including a humidification unit and humidification units.

BACKGROUND

A fan coil apparatus is a component part of many residential, commercial, and industrial heating, ventilation and air conditioning (HVAC) systems, which provide heated air to a room in which they are installed or to multiple rooms. A fan coils comprises a heating and/or cooling heat exchanger and a fan. Air to be heated or cooled is introduced into the heat exchanger and cooled or heated by ambient air that is to be exhausted from the room. The fan coil apparatus may be controlled automatically by a thermostat which may activate the fan coil apparatus as required to maintain a set air temperature in the room.

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figures.

In accordance with one broad aspect of the teachings described herein, which may be used alone or in combination with any other aspect, there is provided a water recovery system for a fan coil assembly which is preferably located in the air exit plenum or passage of a fan coil assembly. The water recovery system comprises a member or members that retain water droplets, which may be micro water droplets and optionally collects some or substantially all or all of the droplets that are not evaporated by air passing through the fan coil assembly.

In accordance with this aspect, there is provided a fan coil apparatus comprising a humidification unit, the humidification unit comprising:
(a) a humidification unit water droplet outlet;
(b) an air permeable water retaining member positioned in an air flow path downstream from a heating zone and downstream from the humidification unit water droplet outlet;
(c) a water impermeable container positioned below the air permeable water retaining member, the water impermeable container having a drain outlet; and,
(d) a drain conduit connected in fluid flow communication with the drain outlet.

In some embodiments, the humidification unit may produce a water mist wherein the water mist enters an air flow stream via the humidification unit water droplet outlet.

In some embodiments, the humidification unit may comprise an ultrasonic humidifier such as a nebulizer.

In some embodiments, the fan coil apparatus may further comprise an air outlet plenum and the humidification unit is located in the plenum.

In some embodiments, the air permeable water retaining member may have a length in a direction transverse to a direction of air flow through the air permeable water retaining member and the humidification unit comprises a mist distributor generally extending in the transverse direction.

In some embodiments, the drain conduit may be connected in fluid flow communication with a drain.

In some embodiments, the humidification unit may further comprise a water mist production member and the drain conduit may be connected in fluid flow communication with the humidification unit at a location upstream of the water mist production member.

In some embodiments, the water mist production member may comprise an ultrasonic humidifier and a water filter upstream of the ultrasonic humidifier and the drain conduit may be connected in fluid flow communication with the humidification unit upstream of the water filter.

In some embodiments, the drain conduit may be connected in fluid flow communication with the humidification unit via a venturi.

In some embodiments, the location upstream of the water mist production member may be positioned below the water impermeable container whereby water drains from the water impermeable container through the drain conduit under the influence of gravity.

In some embodiments, the drain conduit may be connected in fluid flow communication with a water reservoir of the humidification unit.

In some embodiments, the air permeable water retaining member may be seated on the water impermeable container.

In some embodiments, the air permeable water retaining member may be removably receivable from the container.

In accordance with this aspect, there is also provided a humidification unit for a fan coil apparatus, the humidification unit comprising:
(a) a humidification unit water droplet outlet;
(b) an air permeable water retaining member positioned in an air flow path downstream from a heating zone and downstream from the humidification unit water droplet outlet;
(c) a water impermeable container positioned below the air permeable water retaining member, the water impermeable container having a drain outlet; and,
(d) a drain conduit connected in fluid flow communication with the drain outlet.

In some embodiments, the humidification unit may produce a water mist wherein the water mist enters an air flow stream via the humidification unit water droplet outlet.

In some embodiments, the humidification unit may comprise an ultrasonic humidifier such as a nebulizer.

In some embodiments, the air permeable water retaining member may have a length in a direction transverse to a direction of air flow through the air permeable water retaining member and the humidification unit comprises a mist distributor generally extending in the transverse direction.

In some embodiments, the humidification unit may further comprise a water mist production member and the drain conduit may be connected in fluid flow communication with the humidification unit at a location upstream of the water mist production member.

In some embodiments, the water mist production member may comprise an ultrasonic humidifier and a water filter upstream of the ultrasonic humidifier and the drain conduit may be connected in fluid flow communication with the humidification unit upstream of the water filter.

In some embodiments, the drain conduit may be connected in fluid flow communication with the humidification unit via a venturi.

In some embodiments, the location upstream of the water mist production member may be positioned below the water impermeable container whereby water drains from the water impermeable container through the drain conduit under the influence of gravity.

In some embodiments, the drain conduit may be connected in fluid flow communication with a water reservoir of the humidification unit.

In accordance with a second aspect of this disclosure, which may be used alone or in combination with any other aspect, there is provided a mist distributor which is configured to distribute the water droplets, which are preferably micro water droplets such as those produced by an ultrasonic humidifier, across part or all of an air flow path and optionally to collect water droplets that are not entrained or evaporated into the air stream.

In accordance with this second aspect, there is provided a fan coil comprising a humidification unit, the humidification unit comprising:
 (a) a water mist distribution tube having a plurality of outlets;
 (b) a water impermeable container positioned below the water mist distribution tube, the water impermeable container having a drain outlet; and,
 (c) a drain conduit connected in fluid flow communication with the drain outlet.

In some embodiments, the humidification unit may produce a water mist wherein the water mist enters an air flow stream via the plurality of outlets.

In some embodiments, the humidification unit may comprise an ultrasonic humidifier such as a nebulizer.

In some embodiments, the water mist distribution tube may be positioned in an air flow conduit, the air flow conduit may have a length in a direction transverse to a direction of air flow through the air flow conduit and the water mist distribution tube may extend at least substantially along the length of the air flow conduit.

In some embodiments, the water mist distribution tube may extend generally transverse to the direction of air flow through the air flow conduit.

In some embodiments, the water mist distribution tube may be a longitudinally extending tube having first and second opposed ends wherein the water mist distribution tube may extend upwardly from the first end to the second end. In some embodiments, the first end may comprise a water mist inlet end and/or the second end may comprise a water mist inlet end.

In some embodiments, the water mist distribution tube may be a longitudinally extending tube having first and second opposed ends wherein a central portion of the water mist distribution tube may be elevated with respect to the first and second ends.

In some embodiments, the drain conduit may be connected in fluid flow communication with a drain.

In some embodiments, the humidification unit may further comprise a water mist production member and the drain conduit may be connected in fluid flow communication with the humidification unit at a location upstream of the water mist production member.

In some embodiments, the water mist production member may comprise an ultrasonic humidifier and a water filter upstream of the ultrasonic humidifier and the drain conduit may be connected in fluid flow communication with the humidification unit upstream of the water filter.

In some embodiments, the drain conduit may be connected in fluid flow communication with the humidification unit via a venturi.

In some embodiments, the location upstream of the water mist production member may be positioned below the water impermeable container whereby water drains from the water impermeable container through the drain conduit under the influence of gravity.

In some embodiments, the drain conduit may be connected in fluid flow communication with a water reservoir of the humidification unit.

In accordance with this second aspect, there is also provided a humidification unit for a fan coil, the humidification unit comprising:
 (a) a water mist distribution tube having a plurality of outlets;
 (b) a water impermeable container positioned below the water mist distribution tube, the water impermeable container having a drain outlet; and,
 (c) a drain conduit connected in fluid flow communication with the drain outlet.

In some embodiments, the humidification unit may produce a water mist wherein the water mist enters an air flow stream via the plurality of outlets.

In some embodiments, the humidification unit may comprise an ultrasonic humidifier such as a nebulizer.

In some embodiments, the humidification unit may further comprise a water mist production member and the drain conduit may be connected in fluid flow communication with the humidification unit at a location upstream of the water mist production member.

In some embodiments, the water mist production member may comprise an ultrasonic humidifier and a water filter upstream of the ultrasonic humidifier and the drain conduit may be connected in fluid flow communication with the humidification unit upstream of the water filter.

In some embodiments, the drain conduit may be connected in fluid flow communication with the humidification unit via a venturi.

In some embodiments, the location upstream of the water mist production member may be positioned below the water impermeable container whereby water drains from the water impermeable container through the drain conduit under the influence of gravity.

In some embodiments, the drain conduit may be connected in fluid flow communication with a water reservoir of the humidification unit.

In accordance with a third aspect of this disclosure, which may be used alone or in combination with any other aspect, there is provided an air inlet for a humidification unit for a fan coil assembly which uses the blower of the fan coil to provide the air flow across a source of moisture, such as an ultrasonic humidification member. The inlet may be in the form of a scoop or channel that extends into an air flow path, preferably upstream of a heating unit, and guides the air flow into a chamber and across a source of moisture.

In accordance with this third aspect, there is provided a fan coil apparatus comprising a humidification unit, the humidification unit comprising:
 (a) a water mist production member including a chamber wherein, in operation, a water mist produced by the water mist production member is present in the chamber; and,
 (b) an air flow path extending from an air inlet to an air outlet and passing through the chamber, wherein air passing through the air flow path draws water mist from the chamber and out the air outlet, wherein the air inlet comprises a scoop positioned in a first portion of an air flow path of the fan coil apparatus.

In some embodiments, the humidification unit may comprise an ultrasonic humidifier such as a nebulizer.

In some embodiments, the ultrasonic humidifier may be provided in a water tank and the air outlet is provided in an upper portion of the water tank.

In some embodiments, the fan coil apparatus may further comprise a water reservoir upstream of the water tank.

In some embodiments, the fan coil apparatus may further comprise a water filter upstream of the water reservoir.

In some embodiments, the water filter may be selectively connectable in flow communication with a supply of water by an openable valve, wherein the valve is openable when a water level in the water reservoir is low.

In some embodiments, the water reservoir may be selectively connectable in flow communication with a supply of water by an openable valve, wherein the valve is openable when a water level in the water reservoir is low.

In some embodiments, the water reservoir may comprise a float switch that is operatively connectable to the openable valve.

In some embodiments, the water reservoir may be in flow communication with the water tank by gravity feed.

In some embodiments, the air outlet may comprise a plurality of outlets provided in a water mist distribution tube.

In some embodiments, the water mist distribution tube may be provided in a second portion of air flow path of the fan coil apparatus downstream of a location of the scoop, the second portion of air flow path of the fan coil apparatus may have a length in a direction transverse to a direction of air flow therethrough and the water mist distribution tube may extend at least substantially along the length of the second portion of the air flow path.

In some embodiments, the water mist distribution tube may extend generally transverse to the direction of air flow through the second portion.

In accordance with this third aspect, there is also provided a humidification unit for a fan coil apparatus, the humidification unit comprising:
  (a) a water mist production member including a chamber wherein, in operation, a water mist produced by the water mist production member is present in the chamber; and,
  (b) an air flow path extending from an air inlet to an air outlet and passing through the chamber, wherein air passing through the air flow path draws water mist from the chamber and out the air outlet, wherein the air inlet comprises a scoop positionable in a first portion of an air flow path of a fan coil apparatus.

In some embodiments, the humidification unit may comprise an ultrasonic humidifier such as a nebulizer.

In some embodiments, the ultrasonic humidifier may be provided in a water tank and the air outlet is provided in an upper portion of the water tank.

In some embodiments, the fan coil apparatus may further comprise a water reservoir upstream of the water tank.

In some embodiments, the fan coil apparatus may further comprise a water filter upstream of the water reservoir.

In some embodiments, the water filter may be selectively connectable in flow communication with a supply of water by an openable valve, wherein the valve is openable when a water level in the water reservoir is low.

In some embodiments, the water reservoir may be selectively connectable in flow communication with a supply of water by an openable valve, wherein the valve is openable when a water level in the water reservoir is low.

In some embodiments, the water reservoir may comprise a float switch that is operatively connectable to the openable valve.

In some embodiments, the water reservoir may be in flow communication with the water tank by gravity feed.

In accordance with a fourth aspect of this disclosure, which may be used alone or in combination with any other aspect, there is provided a safety control system which shuts of water flow to the humidification unit of a fan coil assembly and optionally, water flow to the fan coil assembly. The safety control system monitors the water level in one or more leak reservoirs and may shut off an inlet valve if a high water level condition occurs.

In accordance with this fourth aspect, there is provided a fan coil comprising a humidification unit, the humidification unit comprising:
  (a) an inner container comprising a water supply for a water mist production member and an inner container water level detector, the inner container water level detector sensing a high water level in the inner container when a water level in the inner container is at a high water level position;
  (b) an outer container comprising a reservoir and an outer container water level detector, wherein the outer container is positioned to receive water which leaks from the inner container, the outer container water level detector sensing a high water level in the outer container when a water level in the outer container is at a high water level position;
  (c) a water supply conduit connectable to a source of water and in fluid flow communication with the inner container; and,
  (d) a shut off valve provided in the water supply conduit, the shut off valve operable between an open position and a closed position,
wherein the shut off valve is in the closed position when the inner container water level detector senses a high water level in the inner container or when the outer container water level detector senses a high water level in the outer container.

In some embodiments, the inner container may be positioned to overlie at least a portion of an open interior of the outer container.

In some embodiments, the outer container may have an inner chamber and the inner container may be at least partially nested in the outer container.

In some embodiments, the inner container water level detector may also sense a low water level in the inner container when a water level in the inner container is at a low water level position and the shut off valve may be in the closed position when the outer container water level detector senses a high water level in the outer container and when the inner container water level detector senses a low water level in the inner container.

In some embodiments, the outer container water level detector may also sense a low water level in the outer container when a water level in the outer container is at a low water level position and the shut off valve may be in the closed position when the inner container water level detector senses a high water level in the inner container and when the outer container water level detector senses a low water level in the outer container.

In some embodiments, the shut off valve may comprise a solenoid.

In some embodiments, at least one of the water level detectors may comprise a float switch.

In some embodiments, the inner container water level detector and the outer container water level detector may each comprise a float switch.

In some embodiments, the outer container may further comprise a drain.

In some embodiments, the water supply of the inner container may comprise a water mist production member chamber and a water reservoir chamber wherein the inner container water level detector is provided in the water mist production member chamber.

In some embodiments, the fan coil may further comprise a separating wall provided between the water mist production member chamber and the water reservoir chamber and the water reservoir chamber may be in flow communication with the water mist production member chamber.

In some embodiments, a fluid flow port may be provided in a lower portion of the separating wall.

In some embodiments, the fluid flow port may be positioned above an upper end of the water mist production member.

In accordance with this fourth aspect, there is also provided a humidification unit for a fan coil, the humidification unit comprising:
  (a) an inner container comprising a water supply for a water mist production member and an inner container water level detector, the inner container water level detector sensing a high water level in the inner container when a water level in the inner container is at a high water level position;
  (b) an outer container comprising a reservoir and an outer container water level detector, wherein the outer container is positioned to receive water which leaks from the inner container, the outer container water level detector sensing a high water level in the outer container when a water level in the outer container is at a high water level position;
  (c) a water supply conduit connectable to a source of water and in fluid flow communication with the inner container; and,
  (d) a shut off valve provided in the water supply conduit, the shut off valve operable between an open position and a closed position,
wherein the shut off valve is in the closed position when the inner container water level detector senses a high water level in the inner container or when the outer container water level detector senses a high water level in the outer container.

In some embodiments, the inner container may be positioned to overlie at least a portion of an open interior of the outer container.

In some embodiments, the inner container water level detector may also sense a low water level in the inner container when a water level in the inner container is at a low water level position and the shut off valve may be in the closed position when the outer container water level detector senses a high water level in the outer container and when the inner container water level detector senses a low water level in the inner container.

In some embodiments, the outer container water level detector may also sense a low water level in the outer container when a water level in the outer container is at a low water level position and the shut off valve may be in the closed position when the inner container water level detector senses a high water level in the inner container and when the outer container water level detector senses a low water level in the outer container.

In some embodiments, at least one of the water level detectors may comprise a float switch.

In some embodiments, the water supply of the inner container may comprise a water mist production member chamber and a water reservoir chamber wherein the inner container water level detector is provided in the water mist production member chamber.

In some embodiments, the humidification unit may further comprise a separating wall provided between the water mist production member chamber and the water reservoir chamber and the water reservoir chamber is in flow communication with the water mist production member chamber.

In some embodiments, a fluid flow port may be provided in a lower portion of the separating wall.

In some embodiments, the fluid flow port may be positioned above an upper end of the water mist production member.

In accordance with a fifth aspect of this disclosure, which may be used alone or in combination with any other aspect, there is provided a leak reservoir system for a water filter for a humidifier. In accordance with this embodiment, a water recovery system comprises a member or members which collect some or substantially all or all of the water that may leak from a water filter assembly of a fan coil assembly.

In accordance with this fifth aspect, there is provided a fan coil comprising a humidification unit, the humidification unit comprising:
  (a) a water filter comprising an inlet connectable to a source of water and a filtered water outlet in flow communication with a downstream portion of the humidification unit;
  (b) a leak container comprising a reservoir and a leak container water level detector, wherein the leak container is positioned to receive water which leaks from the water filter or flow conduits leading to or from the water filter, the leak container water level detector sensing a high water level in the leak container when a water level in the leak container is at a high water level position; and,
  (c) a shut off valve provided in the water supply conduit, the shut off valve operable between an open position and a closed position,
wherein the shut off valve is in the closed position when the leak container water level detector senses a high water level in the leak container.

In some embodiments, the water filter may be positioned to overlie at least a portion of an open interior of the leak container.

In some embodiments, the leak container may have an inner chamber and the water filter may be at least partially nested in the outer container.

In some embodiments, the leak container water level detector may also sense a low water level in the leak container when a water level in the leak container is at a low water level position and the shut off valve may be in the open position when the leak container water level detector senses a low water level in the inner container.

In some embodiments, the shut off valve may comprise a solenoid.

In some embodiments, the water level detector may comprise a float switch.

In some embodiments, the leak container may further comprise a drain.

In some embodiments, the humidification unit may further comprise:
  (a) an inner container comprising a water supply for a water mist production member and an inner container water level detector, the inner container water level detector sensing a high water level in the inner container when a water level in the inner container is at a high water level position, wherein the water supply comprises the downstream portion of the humidification unit; and, (b) an outer container comprising a reservoir and an outer container water level detector, wherein the outer container is positioned to receive water which leaks from the inner container, the outer container water level detector sensing a high water level in the outer container when a water level in the outer container is at a high water level position;

wherein the shut off valve is also in the closed position when the inner container water level detector senses a high water level in the inner container or when the outer container water level detector senses a high water level in the outer container.

In some embodiments:
(a) the inner container water level detector may also sense a low water level in the inner container when a water level in the inner container is at a low water level position;
(b) the leak container water level detector may also sense a low water level in the leak container when a water level in the leak container is at a low water level position; and,
(c) the shut off valve may be in the closed position when the outer container water level detector senses a high water level in the outer container and when the inner container water level detector senses a low water level in the inner container and when the leak container water level detector senses a low water level in the leak container.

In some embodiments:
(a) the outer container water level detector may also sense a low water level in the outer container when a water level in the outer container is at a low water level position;
(b) the leak container water level detector may also sense a low water level in the leak container when a water level in the leak container is at a low water level position; and,
(c) the shut off valve may be in the closed position when the inner container water level detector senses a high water level in the inner container and when the outer container water level detector senses a low water level in the outer container and when the leak container water level detector senses a low water level in the leak container.

In accordance with this fifth aspect, there may also be provided a humidification unit for a fan coil, the humidification unit comprising:
(a) a water filter comprising an inlet connectable to a source of water and a filtered water outlet in flow communication with a downstream portion of the humidification unit;
(b) a leak container comprising a reservoir and a leak container water level detector, wherein the leak container is positioned to receive water which leaks from the water filter or flow conduits leading to or from the water filter, the leak container water level detector senses a high water level in the leak container when a water level in the leak container is at a high water level position; and,
(c) a shut off valve provided in the water supply conduit, the shut off valve operable between an open position and a closed position, wherein the shut off valve is in the closed position when the leak container water level detector senses a high water level in the inner container.

In some embodiments, the water filter may be positioned to overlie at least a portion of an open interior of the leak container.

In some embodiments, the leak container may have an inner chamber and the water filter is at least partially nested in the outer container.

In some embodiments, the leak container water level detector may also sense a low water level in the leak container when a water level in the leak container is at a low water level position and the shut off valve may be in the open position when the leak container water level detector senses a low water level in the inner container.

In some embodiments, the shut off valve may comprise a solenoid.

In some embodiments, the water level detector may comprise a float switch.

In some embodiments, the leak container may further comprise a drain.

In some embodiments, the humidification unit may further comprise:
(a) an inner container comprising a water supply for a water mist production member and an inner container water level detector, the inner container water level detector senses a high water level in the inner container when a water level in the inner container is at a high water level position, wherein the water supply comprises the downstream portion of the humidification unit; and,
(b) an outer container comprising a reservoir and an outer container water level detector, wherein the outer container is positioned to receive water which leaks from the inner container, the outer container water level detector senses a high water level in the outer container when a water level in the outer container is at a high water level position;

wherein the shut off valve is also in the closed position when the inner container water level detector senses a high water level in the inner container or when the outer container water level detector senses a high water level in the outer container.

In some embodiments:
(a) the inner container water level detector may also sense a low water level in the inner container when a water level in the inner container is at a low water level position;
(b) the leak container water level detector may also sense a low water level in the leak container when a water level in the leak container is at a low water level position; and,
(c) the shut off valve may be in the closed position when the outer container water level detector senses a high water level in the outer container and when the inner container water level detector senses a low water level in the inner container and when the leak container water level detector senses a low water level in the leak container.

In some embodiments:
(a) the outer container water level detector may also sense a low water level in the outer container when a water level in the outer container is at a low water level position;
(b) the leak container water level detector may also sense a low water level in the leak container when a water level in the leak container is at a low water level position; and,
(c) the shut off valve may be in the closed position when the inner container water level detector senses a high water level in the inner container and when the outer container water level detector senses a low water level in the outer container and when the leak container water level detector senses a low water level in the leak container.

In accordance with a sixth aspect of this disclosure, which may be used alone or in combination with any other aspect, there is provided a humidifier treatment system to at least partially sterilize and preferably substantially sterilize or sterilize part or all of the humidification system.

In accordance with this sixth aspect, there is provided a fan coil apparatus comprising:
(a) an air flow path extending from a heating zone to a fan coil air outlet and including a humidification section;
(b) a humidification unit comprising a humidification unit water droplet outlet and an air permeable water retaining member, wherein the air permeable water retaining member and the humidification unit water droplet outlet are provided in the humidification section and the air permeable water retaining member is positioned downstream from the humidification unit water droplet outlet; and,
(c) a treatment applicator providing a disinfecting agent upstream from an air outlet of the humidification section.

In some embodiments, the disinfecting agent may comprise one or more of ozone, UV light and hydrogen peroxide.

In some embodiments, the disinfecting agent may comprise ozone and the fan coil further may comprise an ozone destructor material positioned upstream from an air outlet of the fan coil.

In some embodiments, the humidification unit may be located in an air exit plenum of the fan coil.

In some embodiments, the disinfecting agent may be provided in the air exit plenum.

In some embodiments, the disinfecting agent may comprise one or more of ozone and hydrogen peroxide and the disinfecting agent may be introduced into the air exit plenum.

In some embodiments, the disinfecting agent may comprise ozone and the fan coil may further comprise an ozone destructor material positioned downstream from the air permeable water retaining member.

In some embodiments, the disinfecting agent may comprise a UV light source and the UV light source may be located in the air exit plenum.

In accordance with this sixth embodiment, there is also provided a humidification unit for a fan coil apparatus, the humidification unit comprising:
(a) a humidification unit water droplet outlet;
(b) an air permeable water retaining member positioned downstream from the humidification unit water droplet outlet; and,
(c) a treatment applicator providing a disinfecting agent upstream from the air permeable water retaining member.

In some embodiments, the disinfecting agent may comprise one or more of ozone, UV light and hydrogen peroxide.

In some embodiments, the disinfecting agent may comprise ozone and the humidification unit may further comprise an ozone destructor material positioned upstream from an air outlet of the fan coil.

In some embodiments, the disinfecting agent may comprise one or more of ozone and hydrogen peroxide and the disinfecting agent may be introduced into the humidification unit upstream from the air permeable water retaining member.

In some embodiments, the disinfecting agent may comprise ozone and the humidification unit may further comprise an ozone destructor material positioned downstream from the air permeable water retaining member.

14. In some embodiments, the disinfecting agent may comprise a UV light source and the UV light source may be located between the humidification unit water droplet outlet and the air permeable water retaining member.\

BRIEF DESCRIPTION OF THE SEVERAL VIEWS OF THE DRAWINGS

The drawings included herewith are for illustrating various examples of articles, methods, and apparatuses of the teaching of the present specification and are not intended to limit the scope of what is taught in any way.

FIG. 32 is a schematic drawing of a power circuit in accordance with another embodiment.

DESCRIPTION OF VARIOUS EMBODIMENTS

Numerous embodiments are described in this application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", or "fastened" where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. As used herein, two or more parts are said to be "rigidly coupled", "rigidly connected", "rigidly attached", or "rigidly fastened" where the parts are coupled so as to move as one while maintaining a constant orientation relative to each other. None of the terms "coupled", "connected", "attached", and "fastened" distinguish the manner in which two or more parts are joined together.

As used herein and in the claims, a first element is said to be "received" in a second element where at least a portion of the first element is received in the second element unless specifically stated otherwise.

Structure of a Fan Coil Apparatus

The following is a general description of a fan coil having a humidification unit and other features set out herein.

Figure 1:
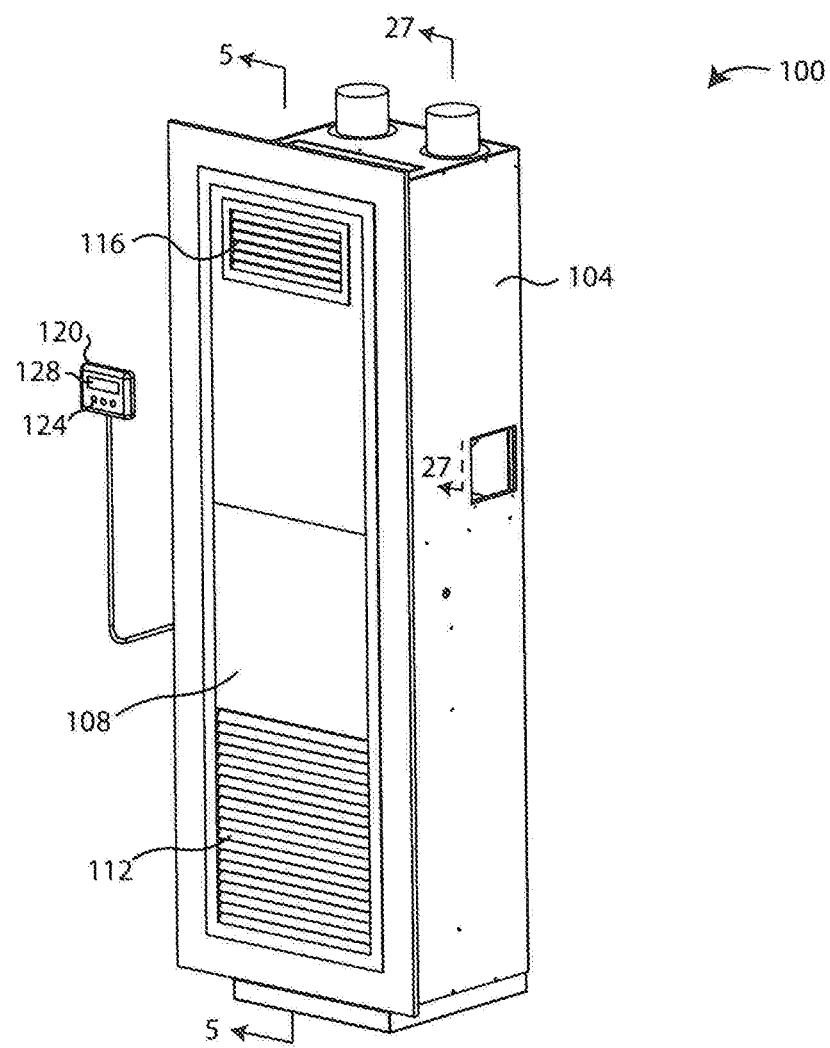
FIG. 1 is a front perspective view of a fan coil apparatus in accordance with an embodiment.
Figure 2:
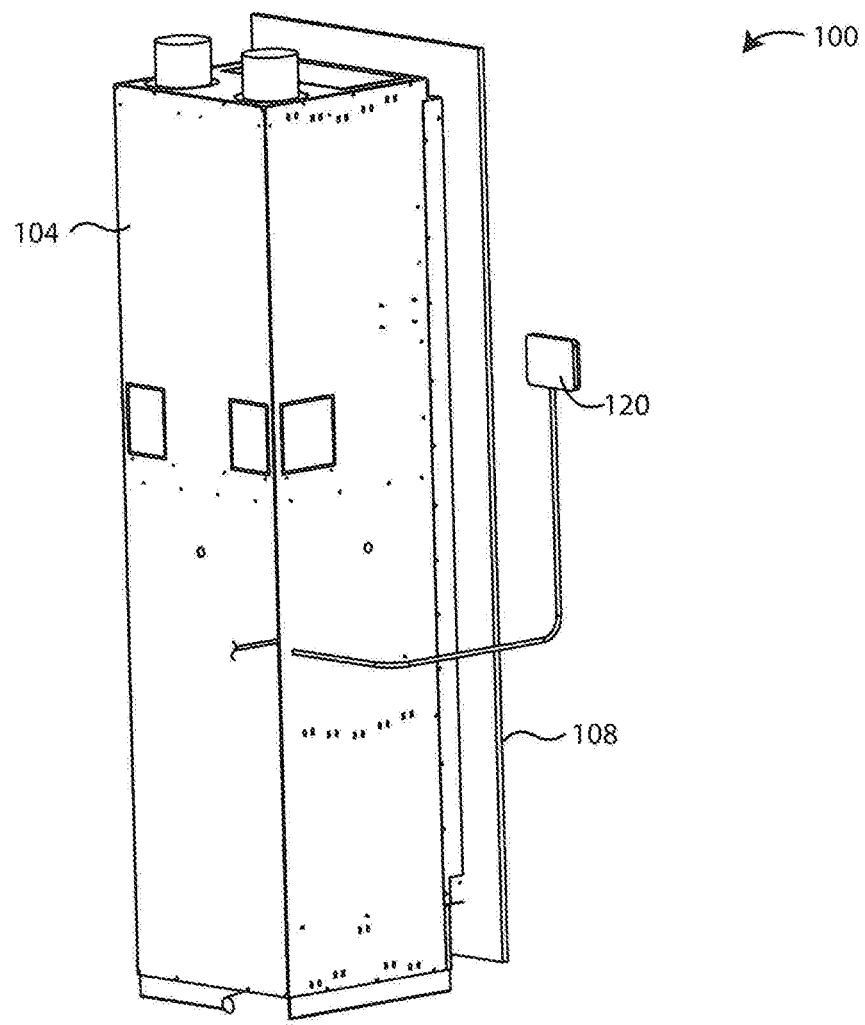
FIG. 2 is a rear perspective view of the fan coil apparatus of FIG. 1.

FIGS. 1 and 2 show a fan coil apparatus 100, in accordance with an embodiment. In the illustrated example, fan coil apparatus 100 includes a housing 104 including a front face 108 defining an air inlet 112 and an air outlet 116. The fan coil apparatus 100 is operable to receive air from air inlet 112, heat or cool the air introduced from inlet 112 and, as selected, humidify the air, and discharge the treated air through air outlet 116 into a room.

The example shown includes a housing 104 that is substantially cuboid (i.e. box-shaped). An advantage of this design is that it provides an efficient and convenient form factor for applications where the fan coil apparatus 100 is recessed into a flat wall. However, in alternative embodiments, fan coil housing 104 can have any size and shape best suited for the intended application.

In the example shown, the fan coil inlet and outlet 112 and 116 are formed in the front face 108 of the fan coil housing 104. This design provides an efficient self-contained apparatus 100 that can be easily accommodated into a room design. However, in alternative embodiments, the fan coil inlet 112, the fan coil outlet 116, or both may be located remotely from the fan coil housing 104. For example, the fan coil outlet 116 may be fluidly connected to the fan coil housing 104 by one or more airflow conduits to allow the fan coil apparatus 100 to service one or more rooms remote from the fan coil apparatus 100 (e.g., via ducting built into a wall or ceiling of a building). In some embodiments, fan coil apparatus 100 may include a plurality of fan coil air inlets 112, a plurality of fan coil air outlets 116, or a plurality of fan coil air inlets 112 and a plurality of fan coil air outlets 116. For example, fan coil apparatus 100 may include a plurality of fan coil air outlets 116 directed to different rooms. This allows one fan coil apparatus 100 to service several rooms.

Still referring to FIGS. 1 and 2, an air regulating device 120 is shown connected to fan coil apparatus 100. The air regulating device 120 may operate as a thermostat and/or a hygrostat, capable of sensing air temperature and/or air humidity, and signaling the fan coil apparatus 100 to generate heated, cooled and/or humidified air in order to maintain the room air at a set temperature and/or humidity. For example, the air regulating device 120 may be programmed to maintain the room air at 21° C. and 40% relative humidity for comfortable human occupancy. Air regulating device 120 can be any thermostat and/or hygrostat device known in the art. In the illustrated embodiment, air regulating device 120 includes inputs 124 for user interaction (e.g. buttons to enter a set air temperature and relative humidity), and an optional display 128 (e.g. to display the current air temperature and relative humidity).

Figure 3:
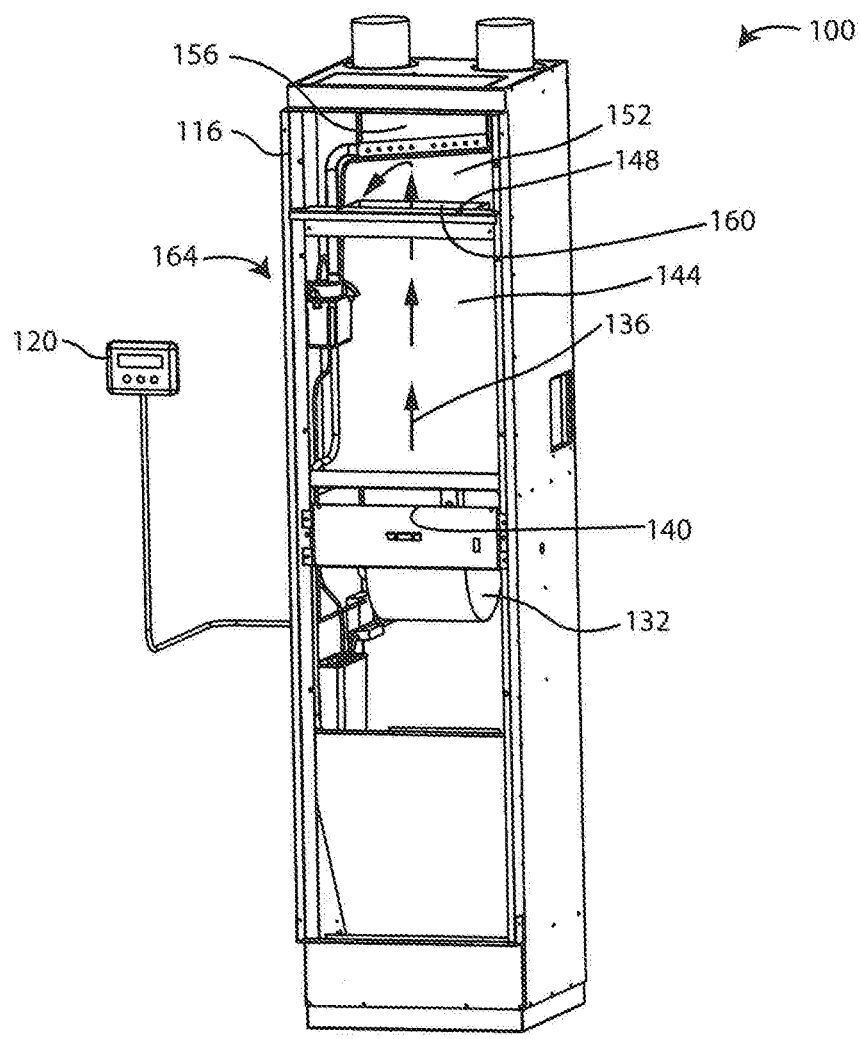
FIG. 3 is a front perspective view of the fan coil apparatus of FIG. 1 with its front face removed.
Figure 4:
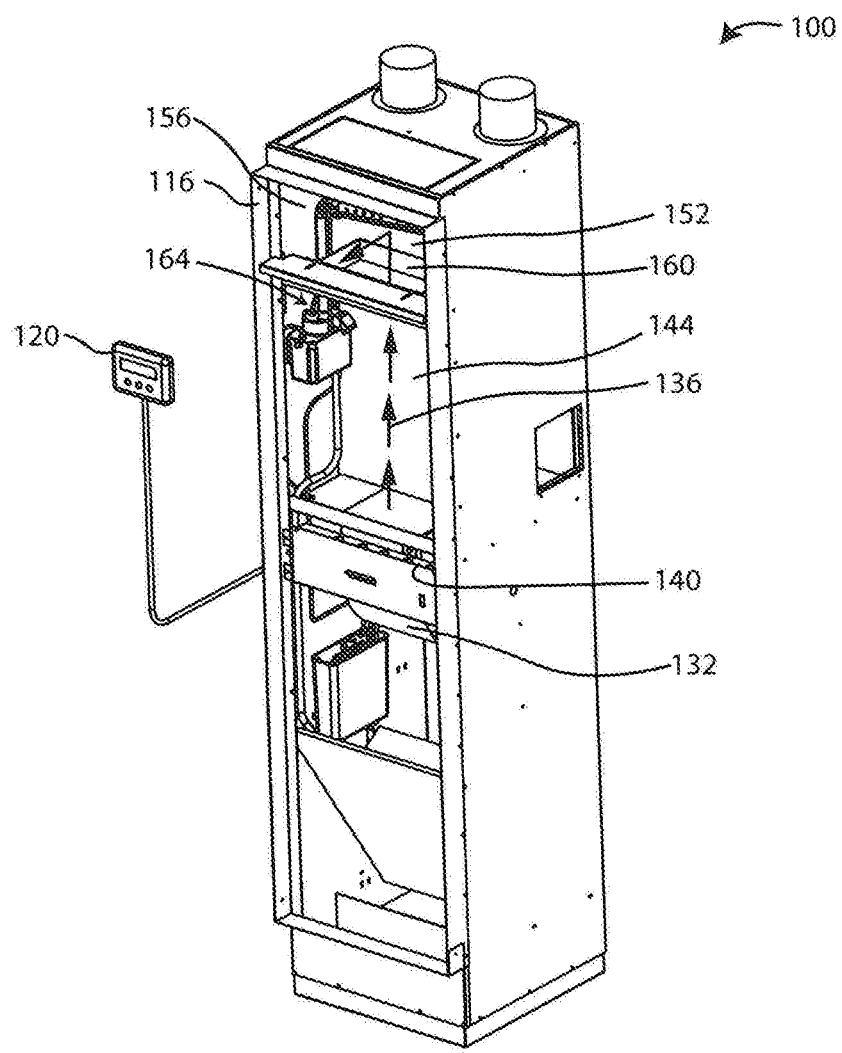
FIG. 4 is a side perspective view of the fan coil apparatus of FIG. 1 with its front face removed.

Reference is now made to FIGS. 3-4 which shows fan coil apparatus 100 with front face 108 (FIG. 1) removed so that some of the internal components are visible. It will be appreciated that the fan coil may be of any design known in the art and may use any flow path, and any heating and air conditioning units known in the heating and cooling arts. As shown, fan coil apparatus 100 includes an air blower 132 and an air flow path 136 which extends from air blower outlet 140 to fan coil air outlet 116. In the illustrated example, the air flow path 136 includes a heating zone 148 between an upstream first portion 144 of fan coil air flow path 136, and a downstream second portion 152 of fan coil air flow path 136. The second portion 152 of the fan coil air flow path 136 may include an air exit plenum 156 positioned upstream of fan coil air outlet 116.

Heating zone 148 can include any air heating device 160 capable of heating the air moving downstream across the heating zone 148. For example, the air heating device 156 can include a heat exchanger as shown, or resistive heating elements, a natural gas burner or the like. In some embodiments, the air heating device 160 includes a heat recovery ventilator (HRV) or an energy recovery ventilator (ERV) that receives heat, or heat and humidity, from exhausted room air for use, e.g., in treating fresh air introduced into the unit from the outside.

Still referring to FIGS. 3 and 4, fan coil apparatus 100 is shown including a humidification unit 164 for humidify air in the fan coil air flow path 136 so that humidified air is discharged from fan coil air outlet 116. When air is heated in heating zone 148, the relative humidity of the air may decrease. The humidity added by humidification unit 164 can help to maintain or increase the relative humidity of the air after heating, such as to attain or maintain a set humidity programmed into air regulating device 120.

Structure of a Humidification Unit

The following is a general description of a humidification unit that may be used in any fan coil apparatus. The following description contains various features which may be used individually or in any combination or sub-combination.

Figure 5:
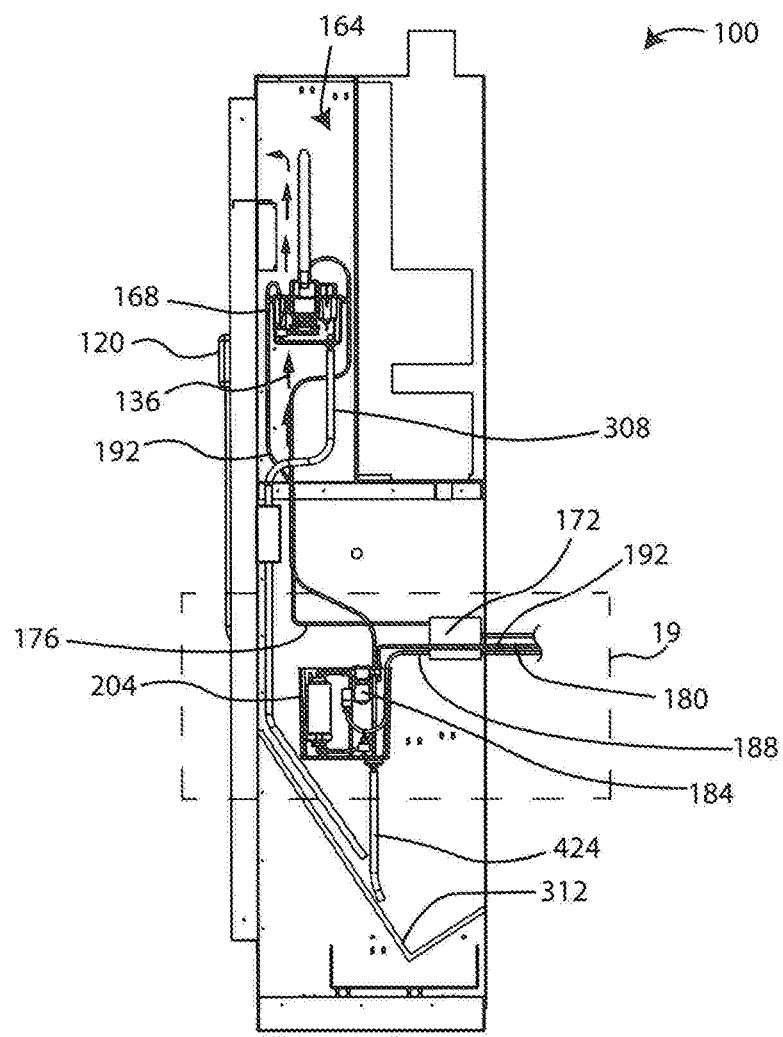
FIG. 5 is a cross-sectional view taken along line 5-5 in FIG. 1.

As exemplified in FIG. 5, humidification unit 164 includes a misting portion 168, and an optional controller 172. The misting portion 168 generates a water mist (e.g. by evaporating or atomizing water), which is exposed to the air flow path 136 in order to humidify the air. The controller 172 directs the activation of misting portion 168. In some embodiments, controller 172 activates misting portion 168 in response to signals from air regulating device 120. For example, controller 172 may activate misting portion 168 in response to signals from air regulating device 120 instructing that humidity is required (e.g. to attain or maintain the set air humidity programmed into air regulating device 120). In some embodiments, controller 172 may determine not to activate misting portion 168 (e.g. determine to keep misting portion 168 deactivated) unless heating device 160 (FIG. 3) has been activated. For example, controller 172 may determine not to activate misting portion 168 unless signals from air regulating device 120 instruct that both humidity and heat is required. An advantage of this design is that water mist is not generated unless the air flow is to be heated. Heating the air flow may reduce its relative humidity and thereby allow the air flow to better absorb the water mist. This can reduce accumulation of water (e.g., agglomerated water droplets in the water mist) inside the fan coil apparatus 100. In alternative embodiments, controller 172 may determine to activate misting portion 168 regardless of whether heating device 160 (FIG. 3) is to be activated as well (e.g., if the blower is operating and a sensor detects that the humidity level is below a desired set point).

Controller 172 regulates the activation of misting portion 168 by controlling the supply of water and/or power to misting portion 168. In the illustrated embodiment, misting portion 168 receives water from a water line 176. Misting portion water line 176 is fluidly coupled to a water supply 180, such as a municipal water line (e.g., a water line in an apartment or condominium) or a reservoir of water (e.g. water tank) external to fan coil apparatus 100. A shut-off valve 184 is positioned in the water flow path upstream of misting portion 168 (e.g. on water line 176, water supply 180, or between water supply 180 and water line 176). The shut-off valve 184 has an open position in which water is allowed to flow past shut-off valve 184 to supply misting portion 168 with water, and a closed position in which shut-off valve 184 prevents the flow of water to misting portion 168. Controller 172 may be communicatively coupled with shut-off valve 184 to direct the position of shut-off valve 184. This allows controller 172 to regulate the supply of water to misting portion 168. Misting portion 168 may run out of water and become unable to generate water mist if the supply of water is stopped.

Shutoff valve 184 can be any valve capable of preventing the flow of water to misting portion 168 in response to electrical or mechanical direction from controller 172. For example, shut-off valve 184 may be an electrical valve (e.g. a solenoid valve), and controller 172 may be communicatively coupled to shut-off valve 184 by electrical line 188, whereby controller 172 can signal shut-off valve 184 to move to the open or closed position. It will be appreciated that any valve may be used.

Still referring to FIG. 5, controller 172 may regulate the supply of power to misting portion 168 to control the activation of misting portion 168. An advantage of this design is that controller 172 can power off misting portion 168 to immediately stop the generation of water mist, even before misting portion 168 runs out of water. Further, shutting off misting portion 168 may prevent damage that may be caused by misting portion 168 operating without any water present. In the illustrated example, misting portion 168 receives electrical power from an electrical line 192. Misting portion electrical line 192 is electrically coupled to a power supply 196, such as a municipal electrical grid (e.g., an electrical outlet or circuit breaker in an apartment or condominium), a power generator, or a power storage device (e.g. battery pack). Controller 172 may be positioned in a circuit between misting portion electrical line 192 and power supply 196 to regulate the supply of power from power supply 196 to misting portion 168. Accordingly, controller 172 may prevent misting portion 168 from receiving power from power supply 196 to deactivate misting portion 168, and allow misting portion 168 to receive power from power supply 196 to activate misting portion 168.

Alternatively, or in addition to controlling misting portion 168 by regulating the supply of power and/or water to misting portion 168, controller 172 may send control signals to misting portion 168 instructing misting portion 168 to activate or deactivate. For example, misting portion 168 may be continuously powered and include logic to receive and act upon control signals to start and stop water mist generation.

In some embodiments, controller 172 regulates not only the activation of misting portion 168 but also the rate of water mist generation by misting portion 168. An advantage of this design is that it allows the rate of water mist generation to be tuned to operate more continuously (and energy efficiently) while maintaining a set air humidity. For example, controller 172 may reduce (but not halt) the flow of water or power to misting portion 168 to slow (but not necessarily stop) the rate of water mist generation. Similarly, controller 172 may send control signals to misting portion 168 instructing misting portion 168 to slow (but not necessarily halt) the rate of water mist generation. Misting portion 168 may include logic to receive and act upon such control signals to vary the rate of water mist generation.

Still referring to FIG. 5, humidification unit 164 may optionally include a filter portion 204. Filter portion 204 may be positioned upstream of misting portion 168 to filter water supplied to misting portion 168 for impurities such as contaminants and minerals, which can accumulate in the misting portion 168 and compromise the operation of misting unit 168 and/or the air quality discharged from fan coil apparatus 100 if dispersed into the generated water mist. In the illustrated example, filter portion 204 is positioned in the water flow path between water supply 180 and misting portion 168. Water delivered from water supply 180 flows through filter portion 204 before being received by misting portion 168.

Figure 6:
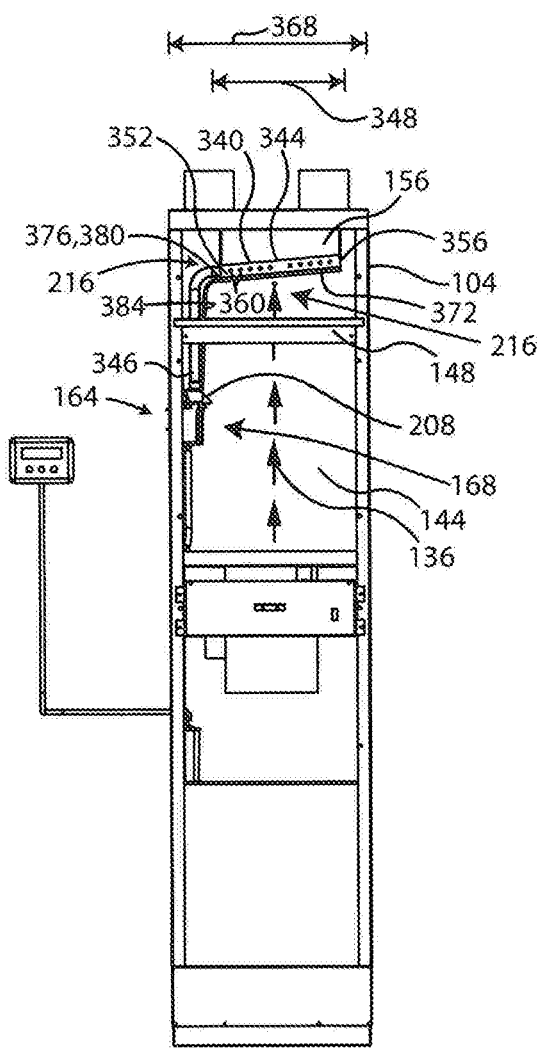
FIG. 6 is a front elevation view of the fan coil apparatus of FIG. 1 with its front face removed.
Figure 7:
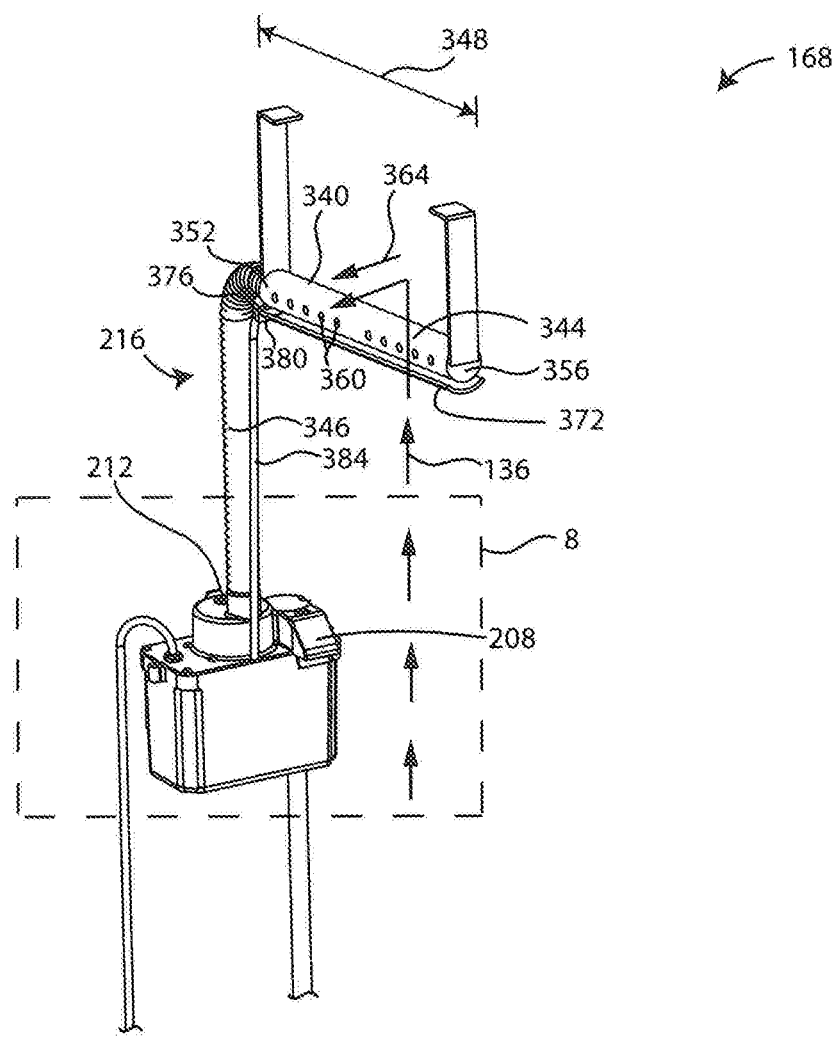
FIG. 7 is a perspective view of a misting portion of a humidification unit.
Figure 8:
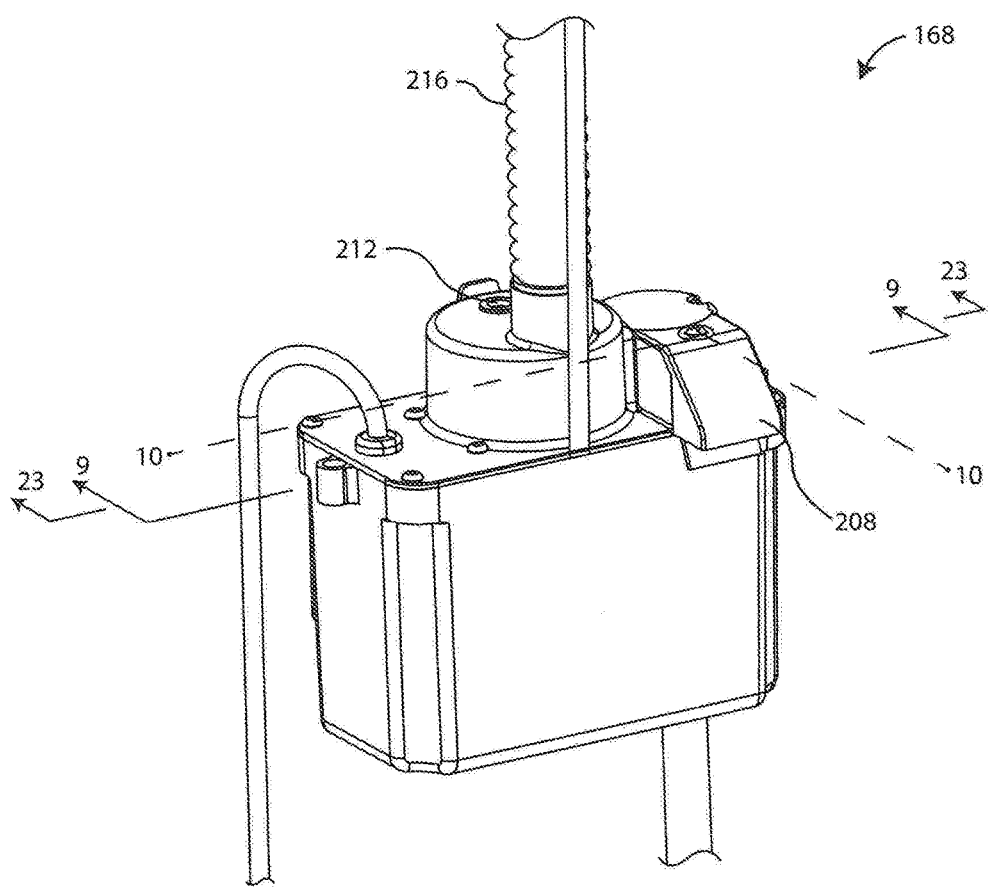
FIG. 8 is an enlargement of region 8 in FIG. 7.
Figure 9:
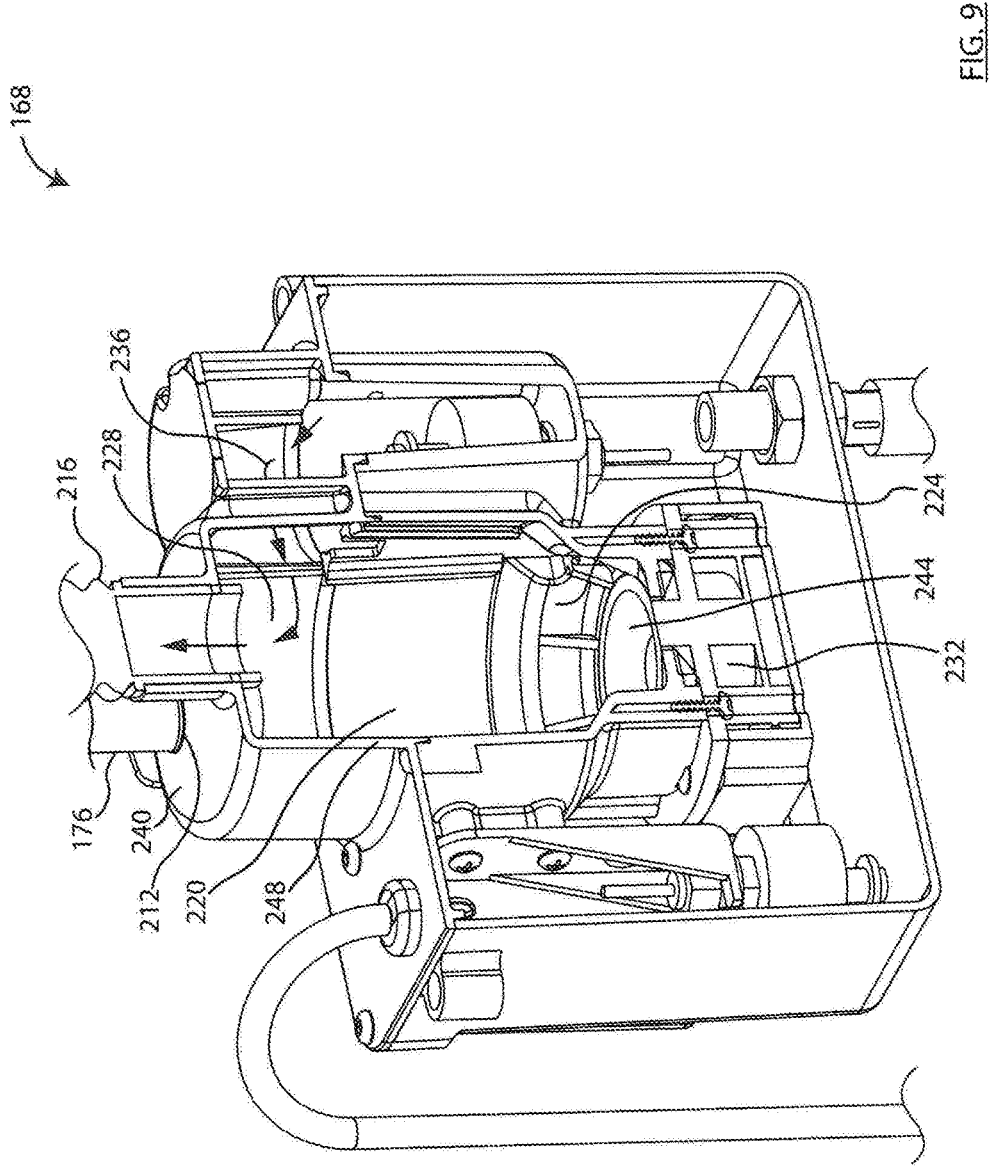
FIG. 9 is a perspective view of the misting portion sectioned along line 9-9 in FIG. 8.

FIGS. 6-8 exemplify a misting portion 168 including an air inlet 208, a water inlet 212, and an air outlet 216. Misting portion air inlet 208 receives air moving downstream in the fan coil air flow path 136. Misting portion 168 generates water mist from water received through misting portion water inlet 212. The generated water mist mixes with air received through misting portion air inlet 208, and then the air and water mist mixture discharges through misting portion air outlet 216 back into the fan coil air flow path 136 to form humidified air that exits through fan coil air outlet 116 into the room.

Production of Air Droplets

The following is a description of an apparatus for producing droplets of air that may be used by itself or in combination with one or more other features disclosed herein including one or more of an air scoop, a misting portion water impermeable container, mist distributor, a filter portion, a leak detection control system, an air permeable water retaining member and a treatment applicator.

In accordance with this embodiment, a water mist production member 232, may be used to produce a water mist (e.g., fine droplets of water) which may be entrained in an air flow. Any water mist production member 232 suitable for generating water mist may be used. In the illustrated embodiment, water mist production member 232 is an ultrasonic device such as a nebulizer 284. Ultrasonic humidifier uses a ceramic diaphragm vibrating at an ultrasonic frequency to create water droplets which, when entrained in an air stream, may form a cool fog. The ultrasonic frequency produces an extremely fine mist of water droplets, e.g., about one micron in diameter, that may be quickly evaporated into an air flow. In alternative embodiments, water mist production member 232 may be an evaporator that includes a water absorptive wick exposed to air flow through the misting portion air flow path 236, or a vaporizer that boils the water to generate steam.

It will be appreciated that, in other embodiments, any apparatus which produces water droplets may be used and, in some embodiments, it will be appreciated that any humidification unit may be used.

As exemplified in FIGS. 9-10, misting portion 168 includes a chamber 220 containing nebulizer 284. Chamber 220 may be of any design which houses a nebulizer 284 or other water mist production member 232 and which provides an air flow path for water droplets to be entrained in an air flow.

As exemplified, chamber 220 includes a water tank 224 positioned below an air plenum 228. Nebulizer 284 may be positioned anywhere inside water tank 224. Preferably, nebulizer 284 is positioned at a lower end 288 of water tank 224 so that nebulizer 284 may remain in contact with water in water tank 224. Nebulizer 284 uses water in the water tank 224 and may cause the water mist to rise into the air plenum 228. In other designs, the air may travel over the water mist production member 232. The water tank 224 is in fluid communication with misting portion water inlet 212. Water tank 224 is resupplied with water from misting portion water inlet 212 as water mist production member 232 consumes water in water tank 224 to generate water mist.

As shown, misting portion chamber 220 may include an upper wall 240 opposite a lower wall 244, and a sidewall 248 extending between the upper wall 240 and lower wall 244. In the illustrated example, water tank 224 is bordered by chamber sidewall 248 and chamber lower wall 244, and air plenum 228 is bordered by chamber sidewall 248 and chamber upper wall 240.

Misting portion water inlet 212 may be positioned anywhere that is in fluid communication with water tank 224. In the illustrated embodiment, misting portion water inlet 212 is positioned above and spaced apart from water tank 224 so that water from water inlet 212 falls by gravity (and water pressure) into water tank 224 below (e.g. across air plenum 228). An advantage of this design is that the backpressure in misting portion water line 176 is constant, which makes the flow rate through misting portion water line 176 easily predictable. In contrast, submerging misting portion water inlet 212 in water tank 224 will result in a backpressure in misting portion water line 176 that varies with the water level in water tank 224. In the illustrated embodiment, misting portion water inlet 212 is positioned in a wall of misting portion chamber 220 that borders air plenum 228. For example, misting portion water inlet 212 may be positioned in chamber upper wall 240 as shown, or chamber sidewall 248.

In alternative embodiments, misting portion water inlet 212 is positioned within water tank 224. This can allow the water level in water tank 224 to be determined by measuring the backpressure in misting portion water line 176.

Misting portion 168 includes an air flow path 236 which extends from misting portion air inlet 208 to misting portion air outlet 216. An air plenum 228 may be positioned in the air flow path 236 between the misting portion air inlet 208 and air outlet 216. This allows the air traveling across the air plenum 228 to entrain or absorb the generated water mist before discharging through the misting portion air outlet 216.

Returning to FIG. 6, misting portion 168 may be positioned anywhere in the fan coil air flow path 136. In the illustrated example, misting portion 168 includes an air inlet 208 positioned in a first portion 144 of fan coil air flow path 136 that is upstream of heating zone 148, and an air outlet 216 that discharges the air and water mist mixture downstream of heating zone 148. An advantage of discharging the air and water mist mixture downstream of heating zone 148 is that the low relative humidity of the heated air allows the water mist to be more efficiently absorbed. As a result, less water mist generation may be required and less water mist may accumulate in the fan coil which may result in rusting of the apparatus or leaking of water from the fan coil apparatus. In turn, the misting portion 168 may consume less power by activating less frequently, activating at a lower power setting, or by including a less powerful water mist production member. Also, less water may be consumed by misting portion 168 because less water is lost. An advantage of positioning misting portion air inlet 208 upstream of heating zone 148 is that cooler air moves through misting portion 168, which makes microorganisms, mold, and the like less likely to cultivate inside misting portion 168.

Air Scoop

The following is a description of an air scoop that may be used by itself or in combination with one or more other features disclosed herein including one or more of a misting portion water impermeable container, mist distributor, a filter portion, a leak detection control system, an air permeable water retaining member and a treatment applicator.

Misting portion air inlet 208 may comprise, consist essentially of or consist of an air scoop 252 which diverts air from the fan coil air flow path 136 to misting portion air flow path 236. An advantage of this design is that air flow through misting portion 168 is driven by the fan coil air blower 132

(FIG. 3), avoiding the need for an additional air moving device to push air through misting portion 168. A further advantage is that the discharge of the air and water vapor mixture from misting portion 168 relies upon the activation of air blower 132 (FIG. 3). The air and water vapor mixture will not discharge from misting portion 168 and stagnantly collect (and accumulate such as by agglomerating into larger water droplets) in air exit plenum 156 (FIG. 3) if the air blower 132 (FIG. 3) is deactivated.

Figure 10:
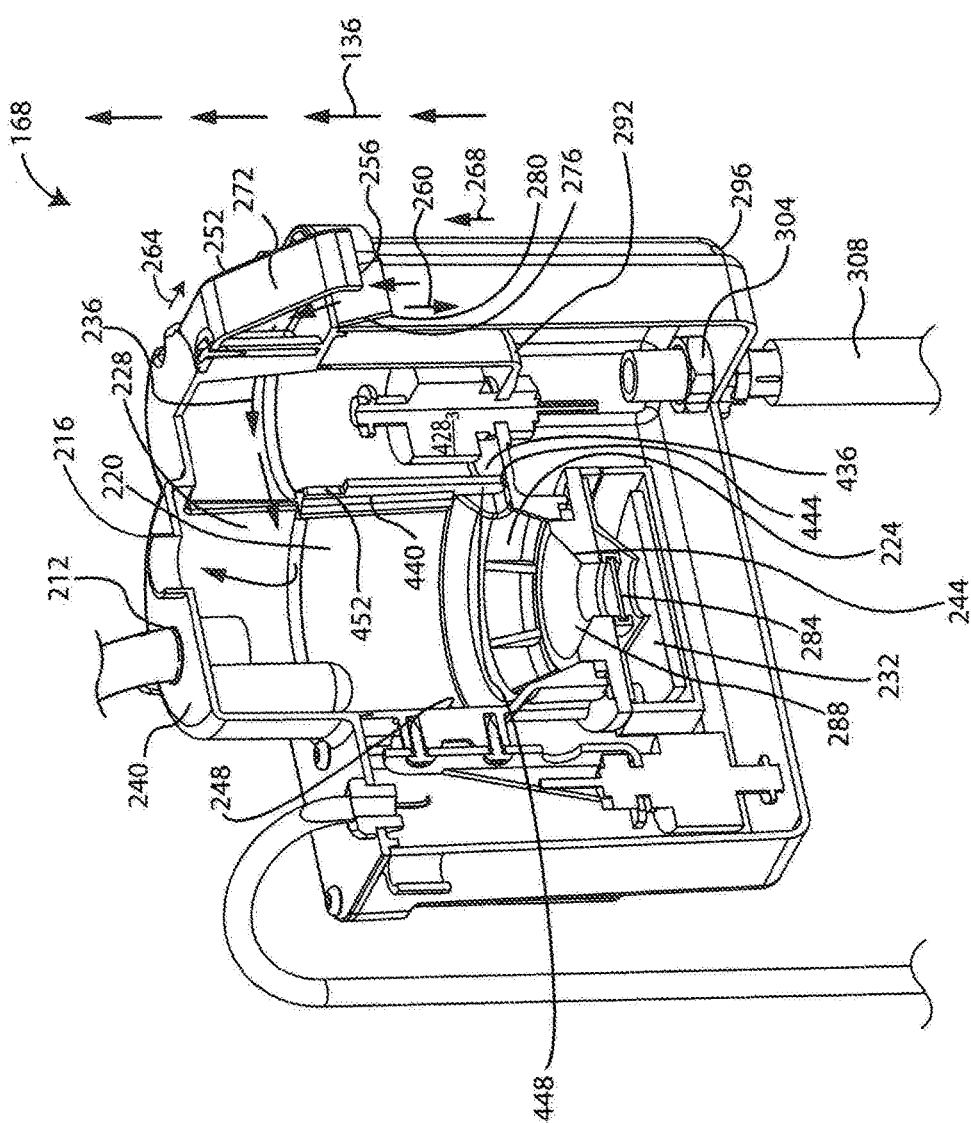
FIG. 10 is a perspective view of the missing portion sectioned along line 10-10 in FIG. 8.

As exemplified in FIG. 10, scoop 252 may include an inlet end 256 that faces in an upstream direction 260 of the fan coil air flow path 136. Scoop 252 may have any configuration suitable for diverting air from fan coil air flow path 136 to misting portion air flow path 236. It will be appreciated that scoop 252 may face directly towards the air flow or it may be at an angle to the air flow path. In the illustrated embodiment, scoop 252 is formed as a hood that extends away from the rest of misting portion 168 in a direction 264 transverse to the downstream direction 268. This provides the scoop inlet end 256 with unobstructed exposure to the air flow moving through fan coil air flow path 136. As shown, scoop 252 may have an upper wall 272 that slopes upwardly in the downstream direction. The sloped upper wall 272 acts to redirect the diverted air into the misting portion chamber 220. Preferably, scoop 252 is configured without any 90 degree bends so as to reduce back pressure through the misting portion.

Still referring to FIG. 10, in some embodiments, scoop 252 may further include an optional air flow limiter 276 that limits the maximum air flow diverted by scoop 252 into misting portion air flow path 236. Air flow limiter 276 prevents excess air velocity through misting portion air flow path 236, which can result in unwanted air turbulence and sloshing of the water in water tank 224, which can result in larger water droplets being entrained in the air flow, which may not be absorbed by the air and may therefore fall out and produce rust or a leak. Similarly, air flow limiter 276 prevents high velocity discharge of the air and water mist mixture at misting portion air outlet 216 against the sidewalls of fan coil apparatus 100 (FIG. 3), which can result in unwanted accumulation of water.

Air flow limiter 276 may have any configuration suitable for limiting the maximum air flow (e.g. maximum air velocity of air diverted) into scoop 252. Preferably, air flow limiter 276 acts passively in response to the air flow impinging on scoop 252. An advantage of this design is that it avoids the need for actuators (e.g. motors), electrical cables, and control devices that may be required by an active air flow limiter. In the illustrated example, air flow limiter 276 comprises a flap that is pivotally (e.g. hingedly) connected at one end to, e.g., the misting unit. Air flow limiter 276 may be movable (e.g. pivotally rotatable) between an open position (shown) and a closed position. In the open position (shown), air flow limiter 276 allows air to enter scoop 252. In the closed position, air flow limiter 276 may partially or completely obstruct air from entering scoop 252. As exemplified, air flow limiter 276 has an upstream face 280 oriented such that air flowing air through fan coil air flow path 136 collides with upstream face 280. The air pressure against air flow limiter upstream face 280 may move the air flow limiter 276 into the closed position when the downstream flow of air through fan coil air flow path 136 exceeds a predetermined flow rate. Accordingly, the air flow limiter may be designed such that it is fully open when air is travelling at a design velocity through air flow path 136. As air travels at a higher rate, the air flow limiter may partially or fully close scoop 252 thereby limiting air flow into the misting unit.

It will be appreciated that, in some embodiments, air flow limiter may be actuated based on, e.g., on an air flow velocity detected by a sensor, and the sensor may send a signal to, e.g., controller 172, which actuals movement or the air flow limiter.

In other embodiments, it will be appreciated that misting portion 168 may include a separate air mover (e.g. blower, not shown). This allows the air flow through misting portion air flow path 236 and fan coil air flow path 136 to be independently controlled. In such an embodiment, a scoop 252 may not be used.

Misting Portion Water Impermeable Container

The following is a description of misting portion water impermeable container that may be used by itself or in combination with one or more other features disclosed herein including one or more of an air scoop, mist distributor, a filter portion, a leak detection control system, an air permeable water retaining member and a treatment applicator.

In accordance with this this feature, a container is positioned to capture water which may leak from tank 224. Accordingly, as exemplified in FIG. 10, in some embodiments misting portion 220 may include an inner container 292 and an outer container 296. As shown, misting portion chamber 220 may be housed in or defined by misting portion inner container 292, and misting portion inner container 292 overlies (at least a portion of) an open interior of misting portion outer container 296. An advantage of this design is that misting portion outer container 296 may collect any water that may leak from misting portion inner container 292 (e.g. if a seal becomes broken). For example, misting portion inner container 292 may be partially and, preferably, substantially or fully nested inside misting portion outer container 296 as shown.

As exemplified, misting portion outer container 296 may include a drain 304 that provides an outlet for water collected in misting portion outer container 296. An advantage of this design is that water leaking from misting portion inner container 292 (e.g. from water tank 224) may be redirected through drain 304 to, e.g. a municipal drain, or recirculated back, e.g., into water tank 224. This prevents the leak water from spilling into the fan coil apparatus 100 and leaking into the fan coil's surroundings (e.g. inside the wall of a room). In the illustrated example, a drain conduit 308 is connected to outer container drain 304 for directing drain water downstream.

As exemplified in FIG. 5 drain conduit 308 may convey drain water toward a fan coil drain 312, which leads outside of fan coil apparatus 100, such as to a municipal drain or outdoors. Alternately, drain water may be recirculated back into misting portion 168 in any manner. As exemplified in FIG. 11 drain conduit 308 conveys drain water to recirculate back into misting portion 168. An advantage of this design is that water consumption is reduced by recycling the drain water instead of discarding the drain water (e.g. to a municipal drain).

Preferably, drain water is recirculated without any additional pumps. As exemplified in FIG. 11, drain conduit 308 directs drain water by gravity downwardly to a venturi device 316 positioned below (i.e. at a lower elevation than) outer container drain 304. Venturi device 316 includes a venturi pipe 320 having a water supply inlet 324, a drain water inlet 328, and an outlet 332. Water supply inlet 324 is fluidly connected downstream of water supply 180, drain water inlet 328 is fluidly connected downstream of outer container drain conduit 308, and venture outlet 332 is fluidly connected upstream of misting portion water inlet 212. In use, the flow of supply water from water supply inlet 324 across venturi pipe 320 to venturi outlet 332 causes a pressure drop which draws in drain water from drain water inlet 328. As a result, a mixture of water supply water and drain water discharges from venturi 320 through venturi outlet 332 towards misting portion water inlet 212.

Figure 11:
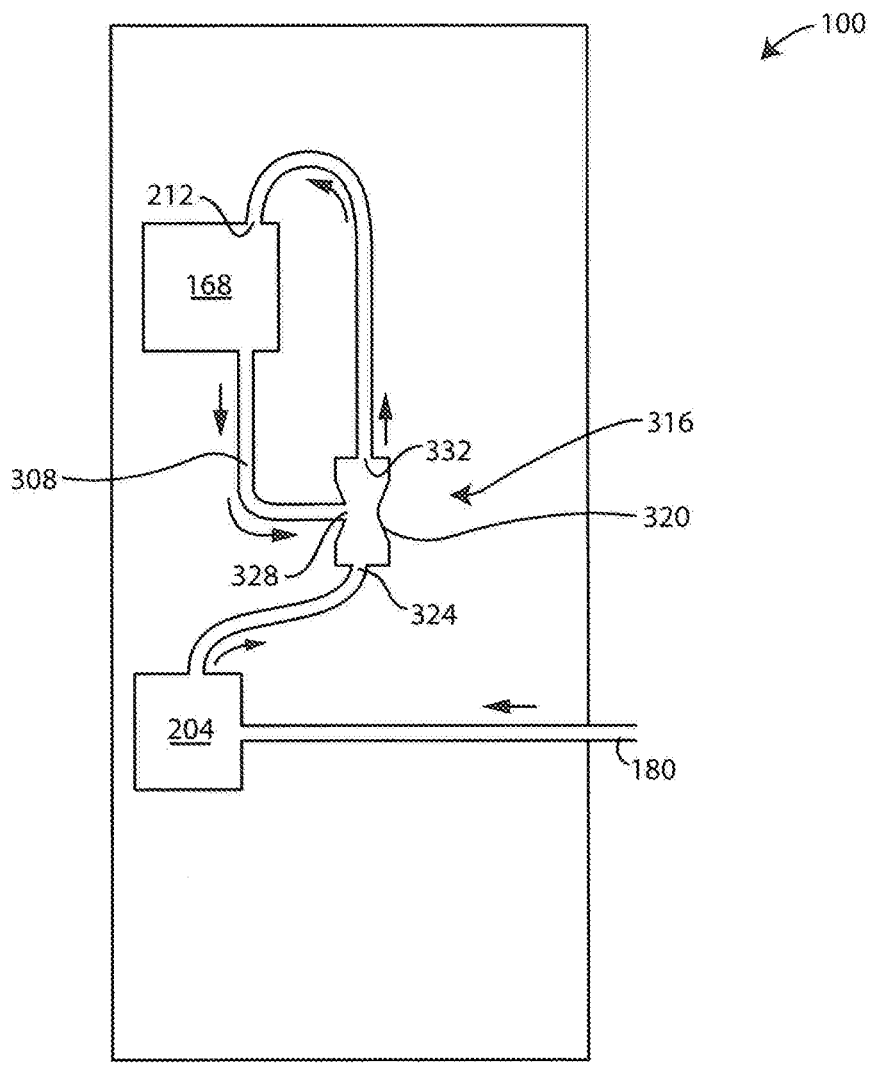
FIG. 11 is a schematic drawing of a fan coil apparatus in accordance with another embodiment.
Figure 12:
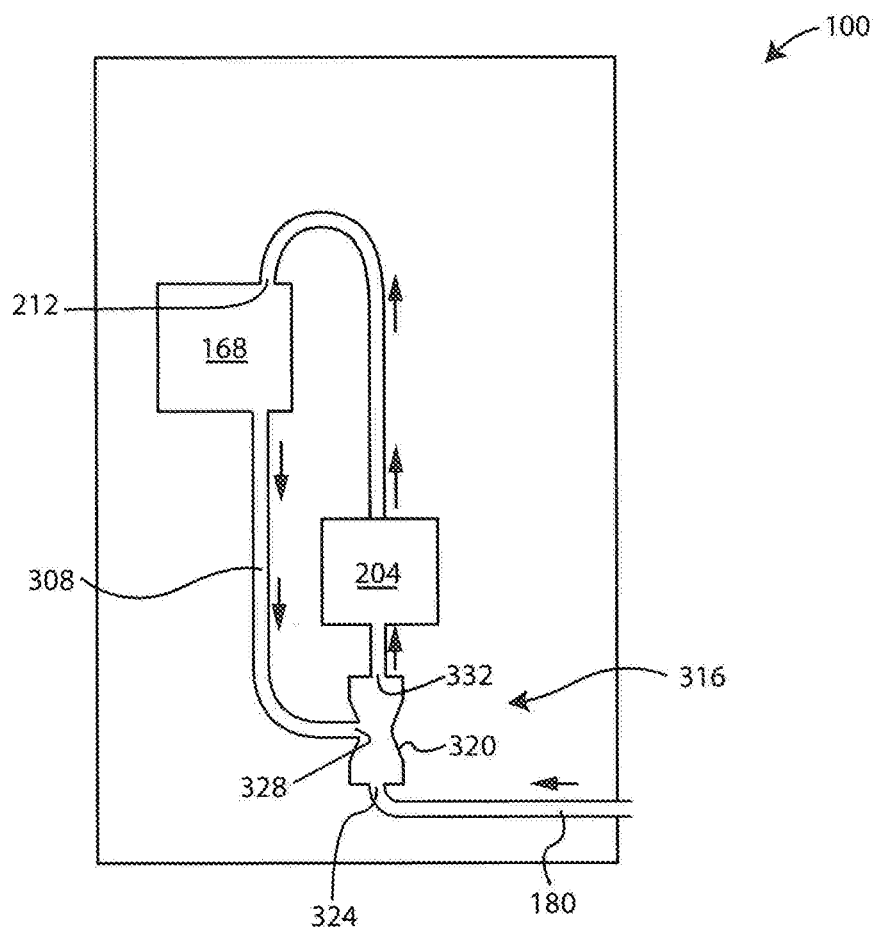
FIG. 12 is a schematic drawing of a fan coil apparatus in accordance with another embodiment.

In the example of FIG. 11, venturi device 316 is positioned upstream of misting portion 168 and downstream of an optional filter portion 204. FIG. 12 shows another example in which venturi device 316 is positioned upstream of an optional filter portion 204 (and therefore upstream of misting portion 168 as well). An advantage of this design is that the drain water may be filtered before returning to misting portion 168.

Figure 13:
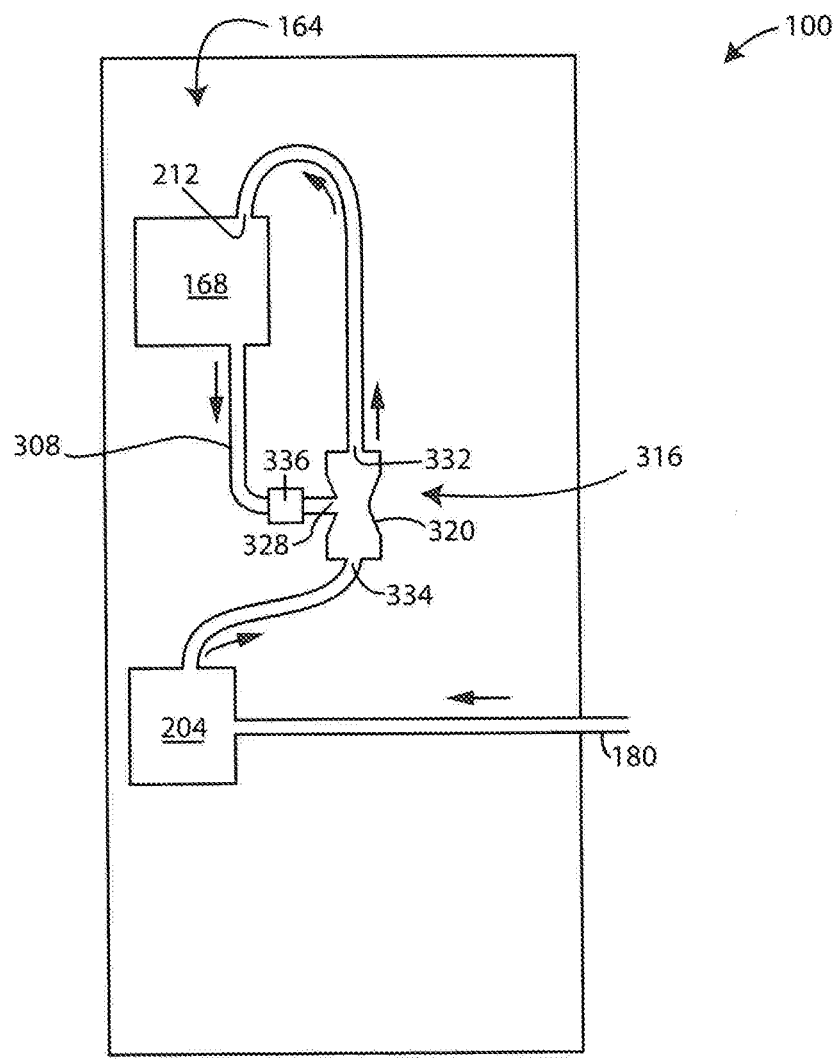
FIG. 13 is a schematic drawing of a fan coil apparatus in accordance with another embodiment.
Figure 14:
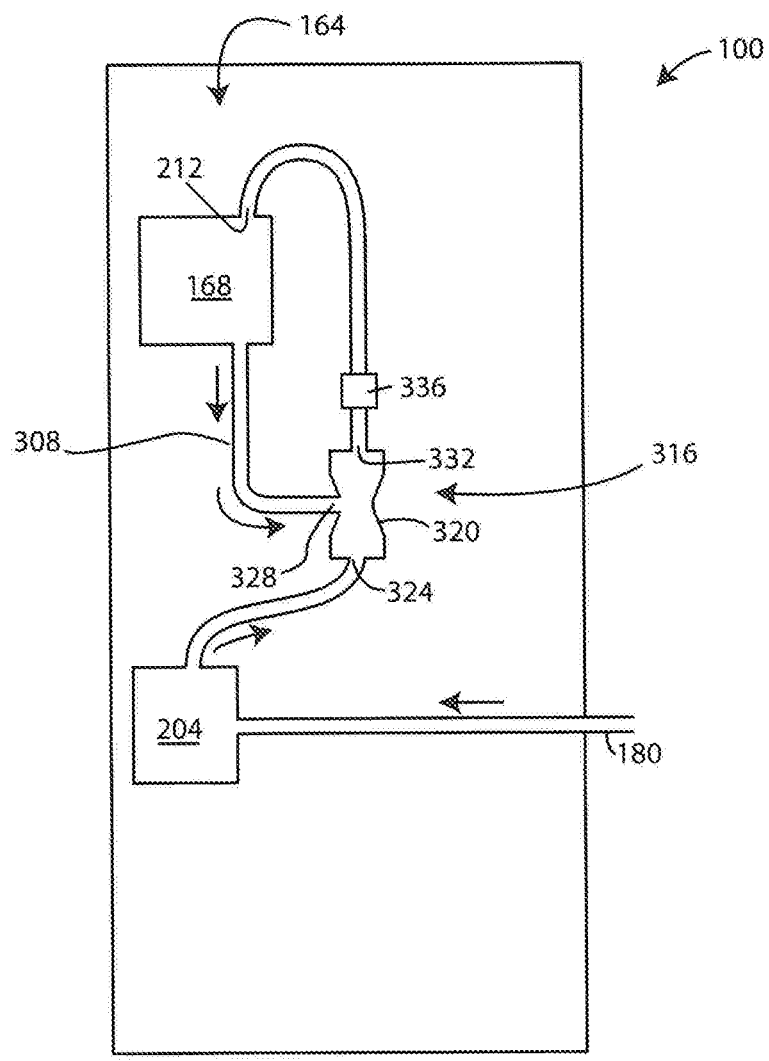
FIG. 14 is a schematic drawing of a fan coil apparatus in accordance with another embodiment.

Referring to FIGS. 13-14, in some embodiments venturi device 316 includes a filter 336 positioned upstream of venturi pipe drain water inlet 328 (as shown in FIG. 13) or positioned downstream of venturi pipe misting portion outlet 332 (as shown in FIG. 14), or both. An advantage of this design is that the drain water is filtered before return to misting portion 168. This may be particularly advantageous where humidification unit 164 does not have a filter portion 204 to route the drain water through to filter the drain water.

Mist Distributor

The following is a description of mist distributor that may be used by itself or in combination with one or more other features disclosed herein including one or more of an air scoop, a misting portion water impermeable container, a filter portion, a leak detection control system, an air permeable water retaining member and a treatment applicator.

In accordance with this feature a mist distributor 340 that distributes the generated water mist into the air moving through the fan coil air flow path 136 is provided, preferably at the air outlet of the fan coil assembly (e.g., misting portion air outlet 216), which may extend part or all of the way across the air flow path and optionally transverse or generally transverse to the air flow direction.

Mist distributor 340 may have any configuration suitable for dispersing the generated water mist into the fan coil air flow path 136. As exemplified in FIGS. 6 and 7, mist distributor 340 comprises a water mist distribution tube 344. As exemplified, misting portion air outlet 216 may also include an air outlet conduit 346 upstream of mist distributor 340 to allow water mist distribution tube 344 to be remotely positioned in the air exit plenum 156 downstream of the heating zone 148.

Water mist distribution tube 344 may be of various configurations. As exemplified in FIG. 7, water mist distribution tube 344 is a longitudinally extending tube having a length 348 extending from a first end 352 to a second end 356. The air and water mist mixture may enter the water mist distribution tube 344 at either end, e.g., first end 352 as exemplified.

As exemplified, water mist distribution tube 344 may have a plurality of outlets 360 distributed along its length 348 and length may extend part or all the way transversely across the air flow path. It will be appreciated that, in some embodiment, two or more distribution tubes 344 may be provided, each of which may extend part or all the way across the air flow path. Further, distribution tube 344 may extend transverse or generally transverse to the direction of air flow or at an angle to the direction of air flow.

As exemplified, water mist distribution tube 344 extends transversely to the air flow direction 364 through fan coil air flow path 136 across water mist distribution tube 344 and may extend part or all the way across the air flow path. For example, as exemplified in FIG. 6, water mist distribution tube 344 may have a transverse length 348 that extends at least substantially along the transverse length 368 of the air flow conduit in which it is positioned. An advantage this design is that the discharged water mist disperses more evenly across the cross-section of the fan coil air flow path 136 for better exposure to the air passing therethrough. As a result, the discharged water mist may be more efficiently absorbed into the air flow so that less water mist may accumulate in the fan coil apparatus. In turn, the misting portion 168 consumes less power by activating less frequently, by activating at a lower power setting, or by including a less powerful water mist production member. Also, less water may be consumed by misting portion 168 because less water is lost to accumulation. Depending on the depth (front to back) of the air outlet, distribution duct may be at an angle to the air flow direction, thereby permitting a longer distribution tube 344.

Figure 17:
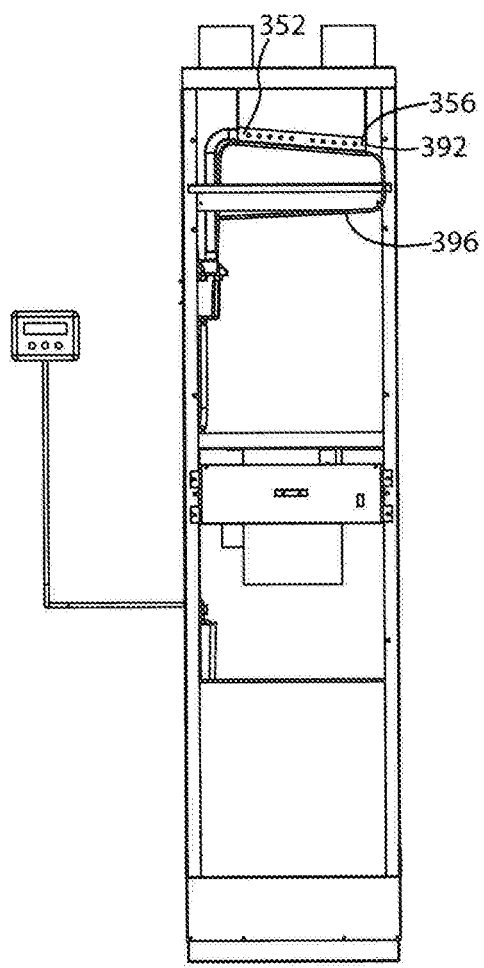
FIG. 17 is a front elevation view of a fan coil apparatus with its front face removed in accordance with another embodiment.
Figure 18:
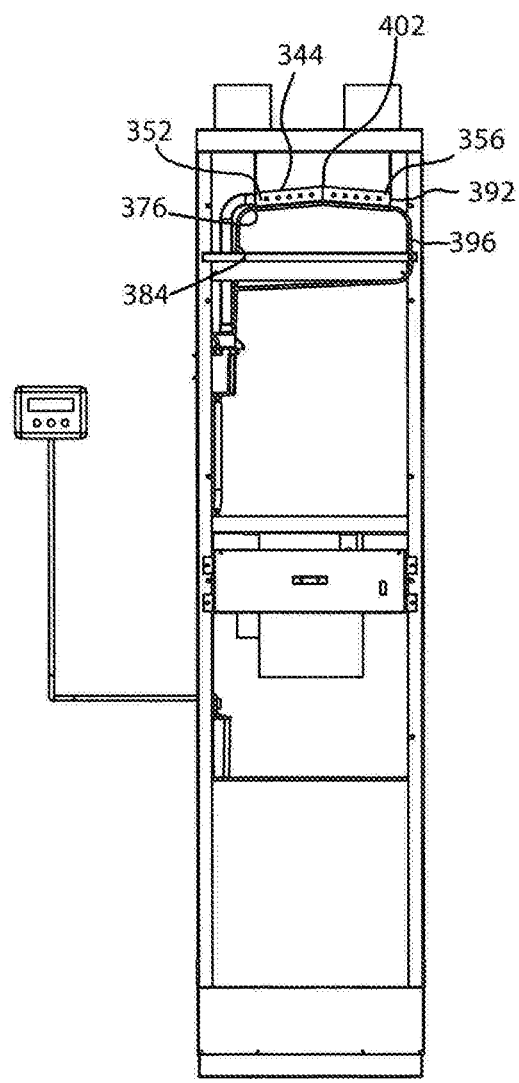
FIG. 18 is a front elevation view of a fan coil apparatus with its front face removed in accordance with another embodiment.

Returning to FIG. 7, distribution tube 344 may include any number of outlets 360. Preferably, distribution tube includes a plurality of outlets 360 to enhance the distribution of water mist into the fan coil air flow path 136. In the illustrated example, distribution tube 344 includes ten outlets 360. Distribution tube outlets 360 may have any size and shape suitable for discharging the air and water mist mixture into the fan coil air flow path 136. For example, in other embodiments, water mist distribution tube 344 may have one or more longitudinally extending openings or slits or a plurality of slits, each of which may extend part way along length 348. Water mist distribution tube 344 may have one or more outlets of any size which permit the air travelling through the misting unit to exit into the air flow path. In the illustrated example, each distribution tube outlet 360 is equally sized and shaped as a small circular perforation in the hollow distribution tube 344. An advantage of this design is that the air and water mist mixture may discharge relatively equally from each distribution tube outlet 360. In alternative embodiments, distribution tube outlet 360 may include outlets 360 of different sizes, different shapes, or both. An advantage of this design is that the size and shape of each distribution tube outlet 360 may be selected to correspond with the shape and flow characteristics of the fan coil air flow path 136. For example, distribution tube outlets 360 nearer to the walls of the fan coil housing 104 (FIG. 6) may be sized and shaped to discharge less water mist than the more centrally located outlets 360 to reduce accumulation on the fan coil housing 104.

Distribution tube outlets 360 may be distributed across all or any portion of the air conduit transverse length 368. Preferably, distribution tube outlets 360 extend across at least 50%, 60%, 70%, 80%, 90% or more of air conduit transverse length 368, as shown. An advantage of this design is that it allows the water mist discharged from the distribution tube outlets 360 to be more evenly distributed across the fan coil air flow path 136.

Water droplets may accumulate in water mist distribution tube 344. Therefore, distribution tube 344 may be sloped to direct the flow of accumulated water droplets inside of distribution tube 344 away from outlets 360. An advantage of this design is that water may be inhibited from dripping out of outlets 360 of distribution tube 344. As exemplified in FIG. 6, distribution tube second end 356 is elevated above distribution tube first end 352. An advantage of this design is that water droplets that accumulate from the air and water mist mixture may flow by gravity towards distribution tube first end 352, through misting portion air outlet conduit 346, into water tank 224. This recycles the accumulated water to be reused for mist generation. FIG. 17 shows an example in which distribution tube first end 352 is elevated above distribution tube second end 356. In this example, distribution tube second end 356 may be open to form a drain 392. As shown, distribution tube drain 392 may be connected to a drain conduit 396 for directing drain water downstream to, e.g. a municipal drain or recirculation back into misting portion, as described above with respect to drain 376 and drain conduit 384 (FIG. 7). FIG. 18 shows an example in which water mist distribution tube 344 includes a central portion 402 located between and elevated above distribution tube first and second ends 352 and 356. In this example, some water droplets that are not evaporated may flow towards distribution tube first end 352 and others towards distribution tube second end 356. In other embodiments, it will be appreciated that distribution tube 344 may extend horizontally or in any other direction or directions.

Optionally, as exemplified in FIGS. 6-7, in some embodiments humidification unit 164 may be configured with a water impermeable container 372 positioned below (i.e. at a lower elevation than) mist distributor 340. The water impermeable container 372 may be positioned below outlets 360 to catch dripping water droplets, accumulated from the discharging air and water mist mixture. An advantage of this design is that it prevents the water droplets from pooling inside fan coil housing 104 and potentially leaking in the apparatus surroundings (e.g. inside the wall in which apparatus 100 is recessed).

Water impermeable container 372 may have any configuration suitable for catching and optionally draining away accumulated water from mist distributor 340. In the illustrated example, water impermeable container 372 is formed as an angled trough having a drain outlet 376 at its lower end 380. Water collected in water impermeable container 372 will flow by gravity downwards to drain outlet 376, which discharges the collected water (also referred to as drain water) downstream to, e.g. a municipal drain, or recirculation back into misting portion 168. An advantage of recirculating the collected water back into misting portion 168 is that the reused water reduces water consumption by displacing water otherwise drawn from water supply 180 (FIG. 3). In the illustrated example, a drain conduit 384 is connected to drain outlet 376 for directing drain water downstream.

Figure 15:
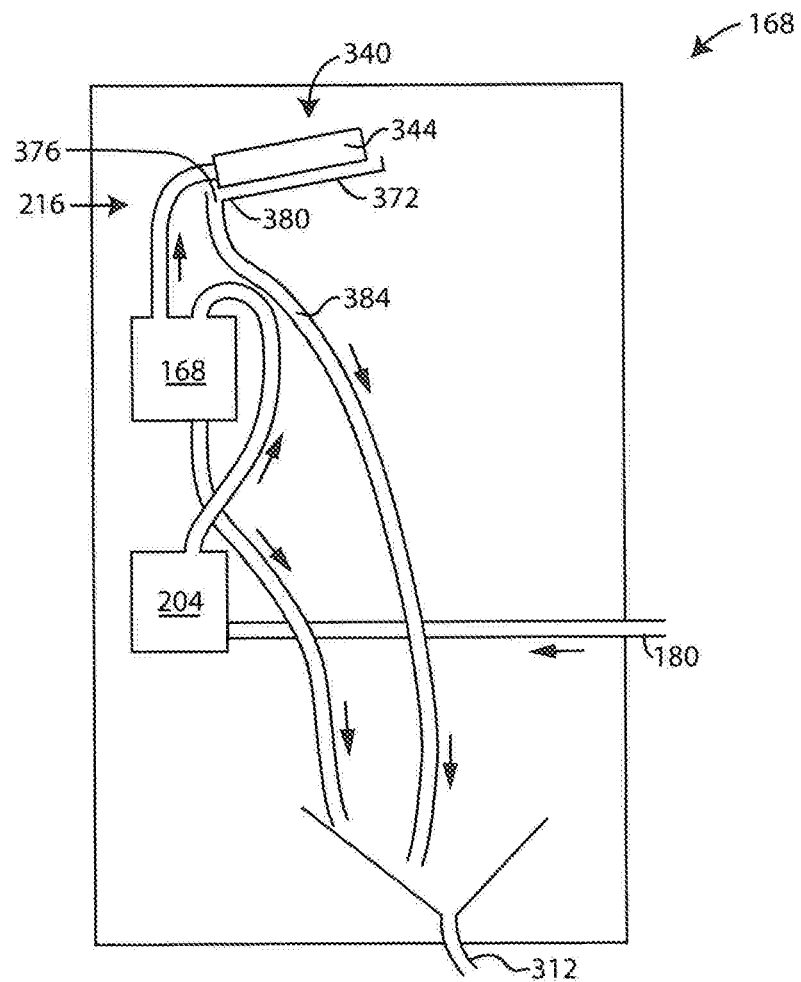
FIG. 15 is a schematic drawing of a fan coil apparatus in accordance with another embodiment.
Figure 16:
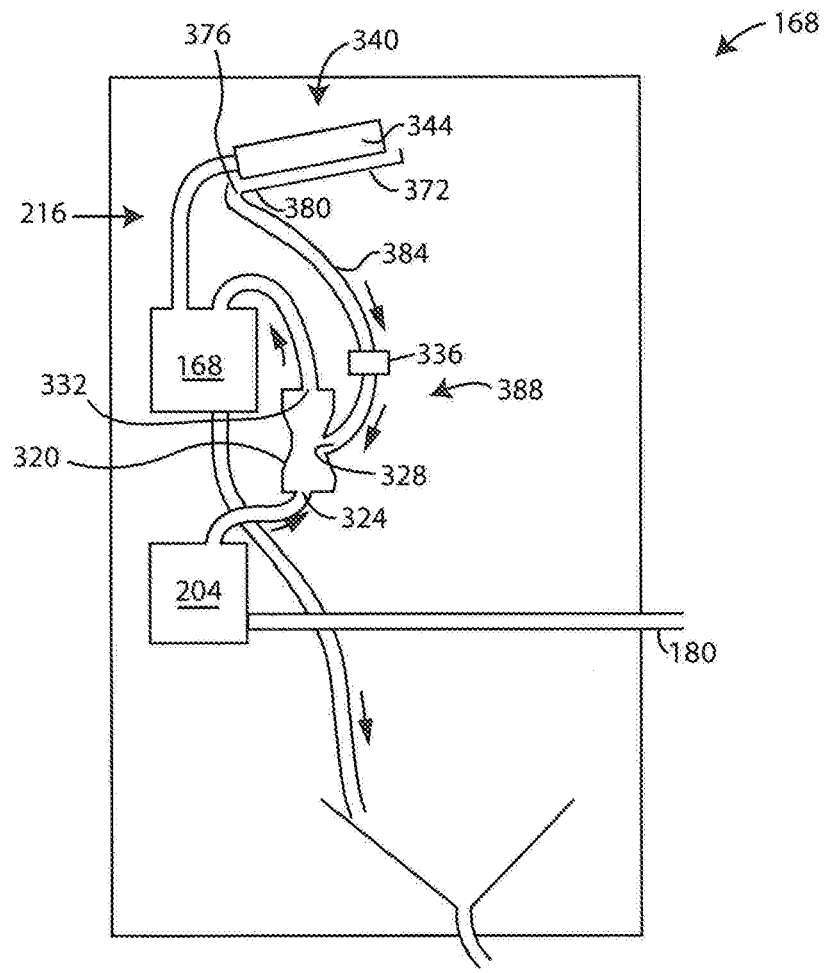
FIG. 16 is a schematic drawing of a fan coil apparatus in accordance with another embodiment.

FIG. 7 shows an example in which drain conduit 384 directs drain water directly into the water tank of misting portion 168 to use in generating water mist. FIG. 15 shows an example in which drain conduit 384 directs drain water toward fan coil drain 312, which leads outside of fan coil apparatus 100, such as to a municipal drain or outdoors. FIG. 16 shows an example in which drain conduit 384 directs collected water to a venturi device 388 upstream of filter portion 204. Venturi device 388 is substantially similar to venturi device 316 (FIG. 11), and includes a venturi pipe 320 having a water supply inlet 324, a drain water inlet 328, and a misting portion outlet 332. Water supply inlet 324 is fluidly connected downstream of water supply 180, drain water inlet 328 is fluidly connected downstream of drain outlet 376, and misting portion outlet 332 is fluidly connected upstream of misting portion 168, such as downstream of filter portion 204 as shown. Venturi device 388 may also include a filter 336 positioned upstream of drain water inlet 328 or downstream of misting portion outlet 332.

Air Permeable Water Retaining Member

The following is a description of an air impermeable water retaining member that may be used by itself or in combination with one or more other features disclosed herein including one or more of an air scoop, a misting portion water impermeable container, mist distributor, a filter portion, a leak detection control system, and a treatment applicator.

In accordance with this feature, humidification unit 164 may include an air permeable water retaining member 456 positioned in the fan coil air flow path 136 downstream of mist distributor 340. The air permeable water retaining member 456 allows the humidified air flow to pass through and retain (e.g., adsorbs, adsorbs or physically retains) excess water emitted from the distributor 340 that is not entrained or evaporated into the humidified air flow. An advantage of this design is that liquid water in the air flow is removed from the air flow instead of pooling in fan coil housing 104, a downstream air flow vent, or a room serviced by fan coil apparatus 100.

Figure 27:
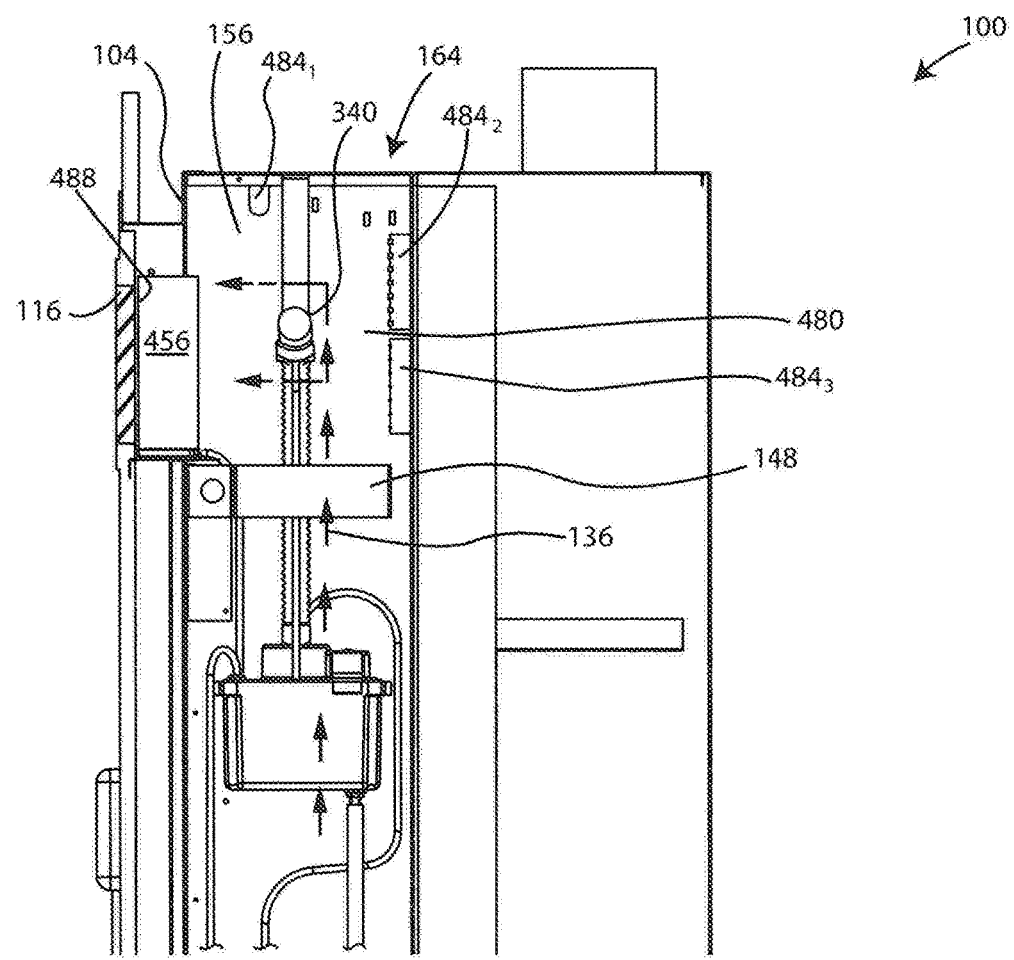
FIG. 27 is a cross-sectional view taken along line 27-27 in FIG. 1.

As exemplified in FIG. 27, air permeable water retaining member 456 may be positioned anywhere in the fan coil air flow path 136 downstream of mist distributor 340. Preferably, air permeable water retaining member 456 is spaced apart from mist distributor 340 sufficiently to allow the discharged water mist an opportunity to evaporate into the air flow. In the illustrated example, air permeable water retaining member 456 is positioned in the air exit plenum 156 immediately upstream of fan coil air outlet 116. An advantage of this design is that water mist discharged from mist distributor 340 is given an extended opportunity to evaporate into the air flow before the remaining liquid phase water is removed from the air flow by air permeable water retaining member 456.

Air permeable water retaining member 456 may be mounted in position in the fan coil air flow path 136 in any suitable manner. As exemplified in FIGS. 28 and 29, humidification unit 164 includes a water impermeable container 460 which holds air permeable water retaining member 456. For example, air permeable water retaining member 456 may be seated on of located above water impermeable container 460. An advantage of this design is that water impermeable container 460 may collect water that flows or drips from air permeable water retaining member 456.

Water impermeable container 460 may have any configuration suitable for holding air permeable water retaining member 456 in position, and/or catching water that flows or drips from air permeable water retaining member 456. In the illustrated example, water impermeable container 460 includes an optional drain outlet 464 that provides an outlet for water collected on water impermeable container 460. An advantage of this design is that water that flows or drips from water impermeable container 460 may be redirected through drain outlet 464 to, e.g. a municipal drain, or recirculated back into misting portion 168. This prevents the water collected on water impermeable container 460 from spilling into the fan coil apparatus 100 and leaking into the fan coil's surroundings (e.g. inside the wall of a room). In the illustrated example, a drain conduit 464 is connected to water impermeable container 460 for directing the drain water downstream.

Drain conduit 464 may be substantially similar to drain conduit 376. As described previously with respect to drain conduit 376, drain conduit 464 may direct drain water towards fan coil drain 312, water tank 224 of misting portion 168, or to filter portion 204 such as by way of a venturi device 388 (FIG. 16). In this regard, the description and drawings relating to drain conduit 376 apply mutatis mutandis to drain conduit 464, and repetitive description and drawings for drain conduit 464 are not provided.

Air permeable water retaining member 456 may be secured or removably secured in position using any support or holding structure. Preferably, air permeable water retaining member 456 overlies (e.g. is positioned above or is seated on) water impermeable container 460 so that water may drip or flow by gravity from air permeable water retaining member 456 to water impermeable container 460. In some embodiments, water impermeable container 460 may be integrally formed with or permanently connected to air permeable water retaining member 456. In the illustrated example, air permeable water retaining member 456 is removably seated (e.g. removably received in) water impermeable container 460. An advantage of this design is that it allows air permeable water retaining member 456 to be removed for cleaning, repair, or replacement should that be required.

Figure 28:
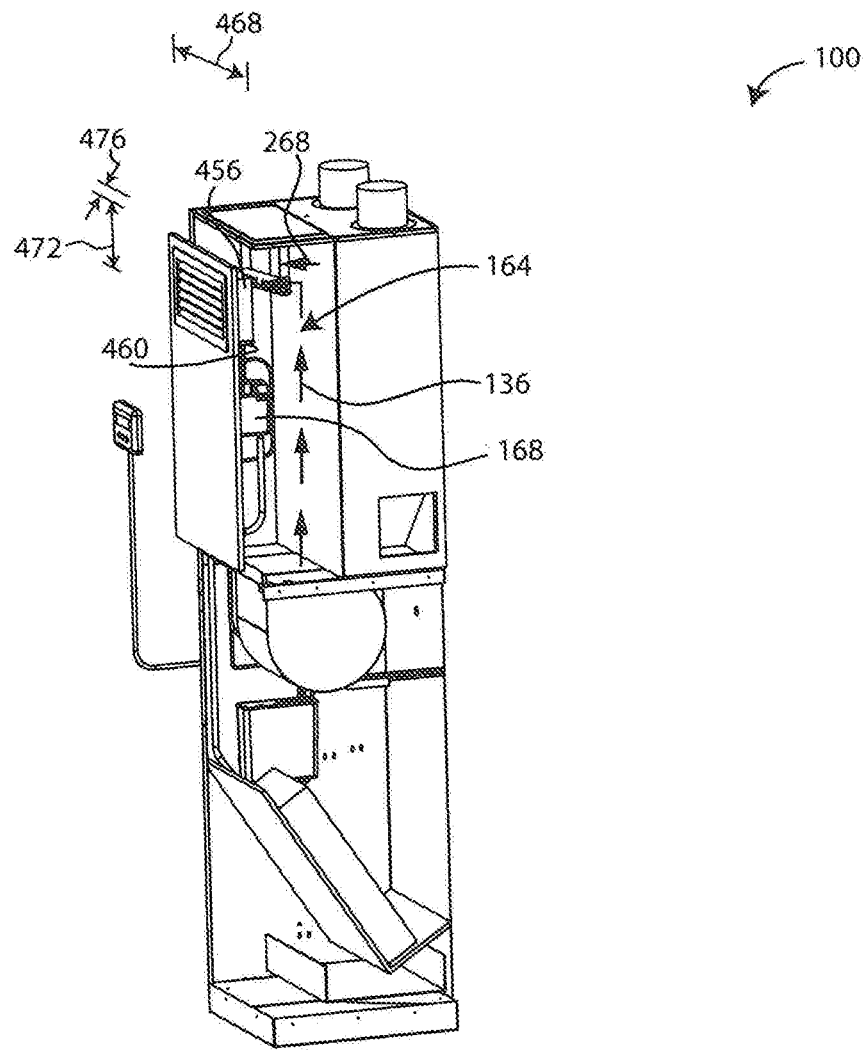
FIG. 28 is a perspective view of the fan coil apparatus of FIG. 1 with part of its housing removed.
Figure 29:
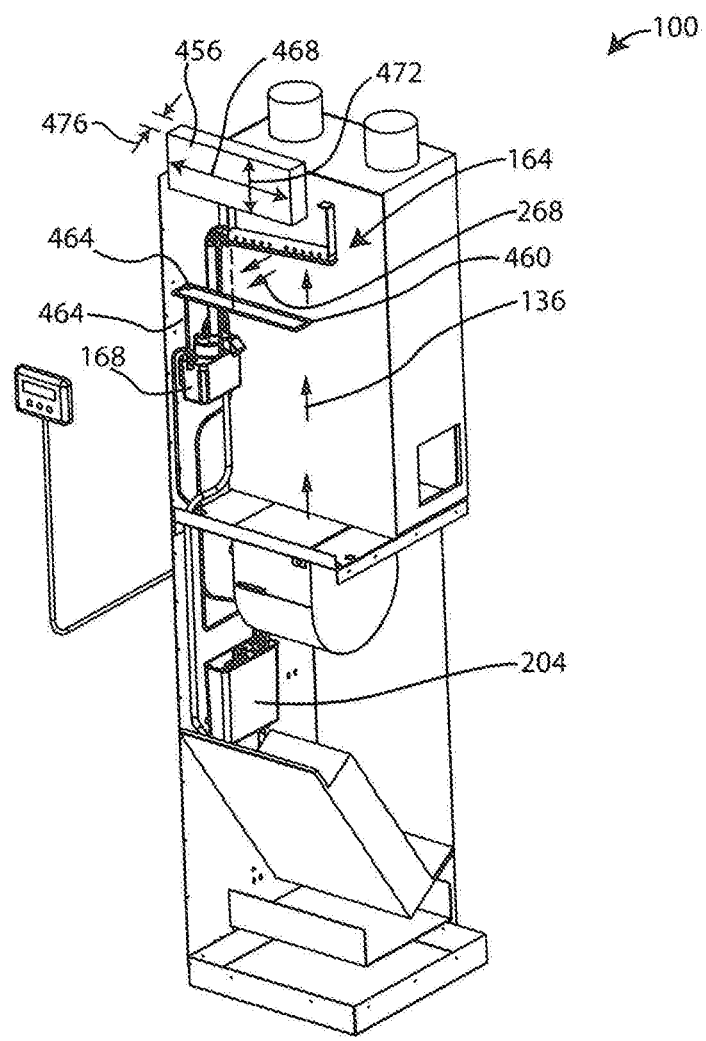
FIG. 29 is a perspective view of the fan coil apparatus of FIG. 1, with an air permeable water retaining member in an exploded position, and an air heating device removed.

Still referring to FIGS. 28-29, air permeable water retaining member 456 can have any size and shape suitable for retaining excess water from the air flow in fan coil air flow path 136. As exemplified, air permeable water retaining member 456 has a length 468 transverse to the fan coil air flow path downstream direction 268, a height 472 transverse to the fan coil air flow path downstream direction 268, and a thickness 476 parallel to the fan coil air flow path downstream direction 268. The length 468 and height 472 may be sized so that air permeable water retaining member 456 spans at least a majority, and preferably substantially the entire cross-section of the fan coil air flow path 136. An advantage of this design is that a majority or substantially all of the air flow through fan coil air flow path 136 may pass through air permeable water retaining member 456, and therefore a majority or substantially all of the excess water can be retained by air permeable water retaining member 456. Thickness 476 is preferably sized to optimize water retention efficiency. If thickness 476 is too great, then air permeable water retaining member 456 may obstruct the air flow through fan coil air flow path 136. If thickness 476 is too thin, then air permeable water retaining member 456 may have too little water retention capacity.

Figure 30:
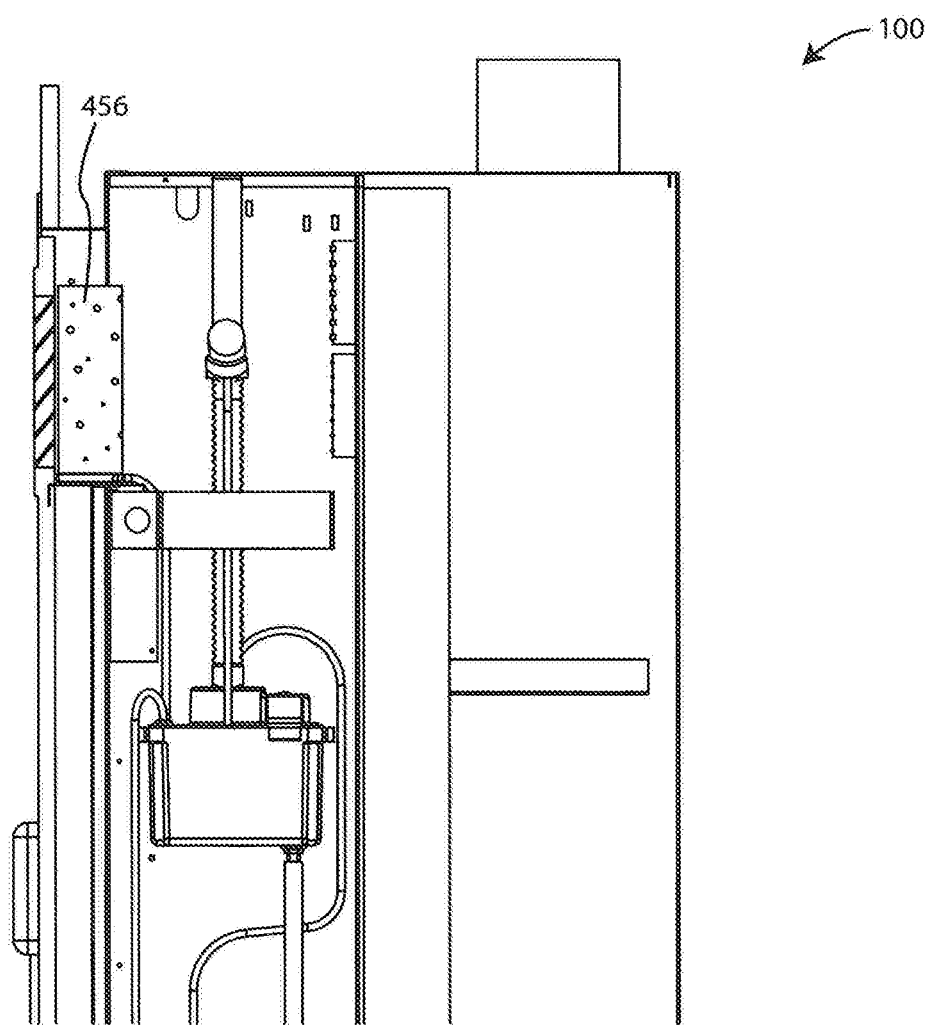
FIG. 30 is a cross-sectional view taken along line 27-27 in FIG. 1 in accordance with another embodiment; and, FIG. 31 is a cross-sectional view taken along line 27-27 in FIG. 1 in accordance with another embodiment.
Figure 31:
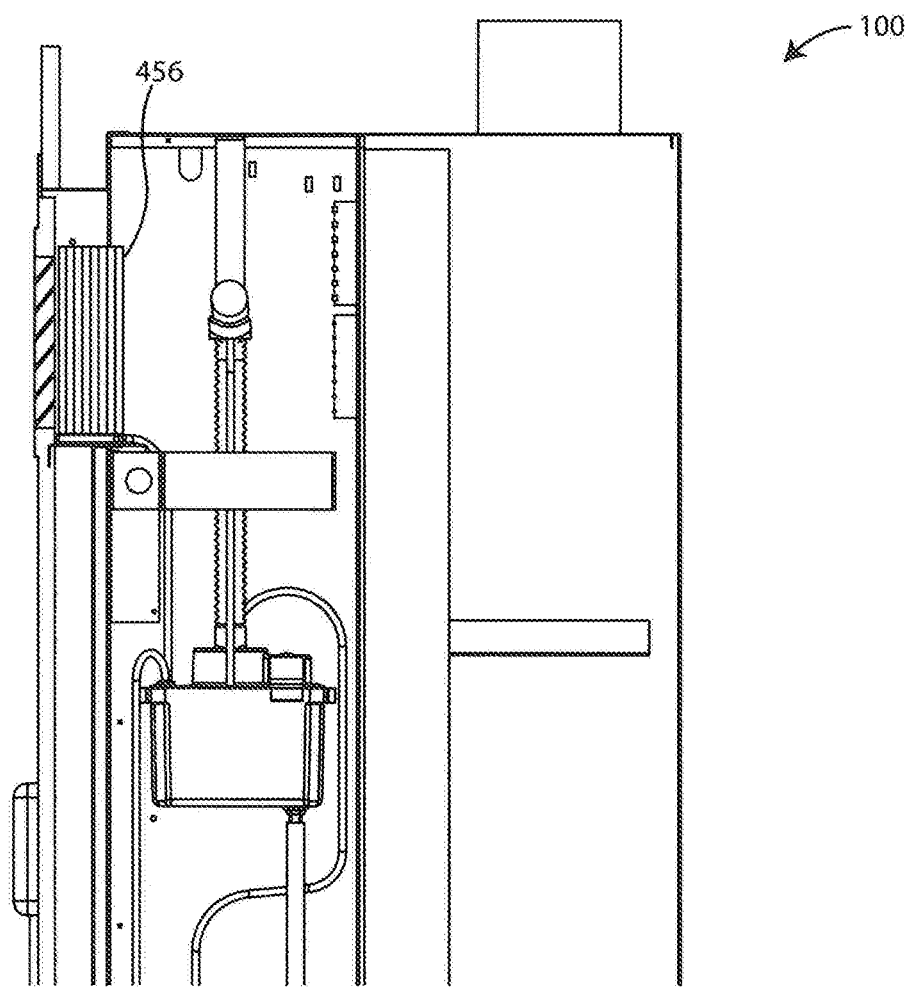

Air permeable water retaining member 456 may be formed of any material suitable for retaining excess water from the air flow in fan coil air flow path 136 and which, preferably, will not rust. For example, air permeable water retaining member 456 may comprise an open cell material, such as an open cell foam (see e.g., FIG. 30), an open cell plastic, an aluminum mesh, aluminum plates or the like. For example, FIG. 31 exemplifies an air permeable water retaining member 456 includes a layered material, such as layered aluminum mesh or layered aluminum plates.

Filter Portion

The following is a description of an filter portion that may be used by itself or in combination with one or more other features disclosed herein including one or more of an air scoop, a misting portion water impermeable container, mist distributor, a leak detection control system, an air permeable water retaining member and a treatment applicator. Optionally, in accordance with this feature, a water filter is provided upstream of the mist production member. An advantage of this design is that, if the mist producing member is a nebulizer or the like, then scaling or fouling of the mist production member may be reduced.

Figure 19:
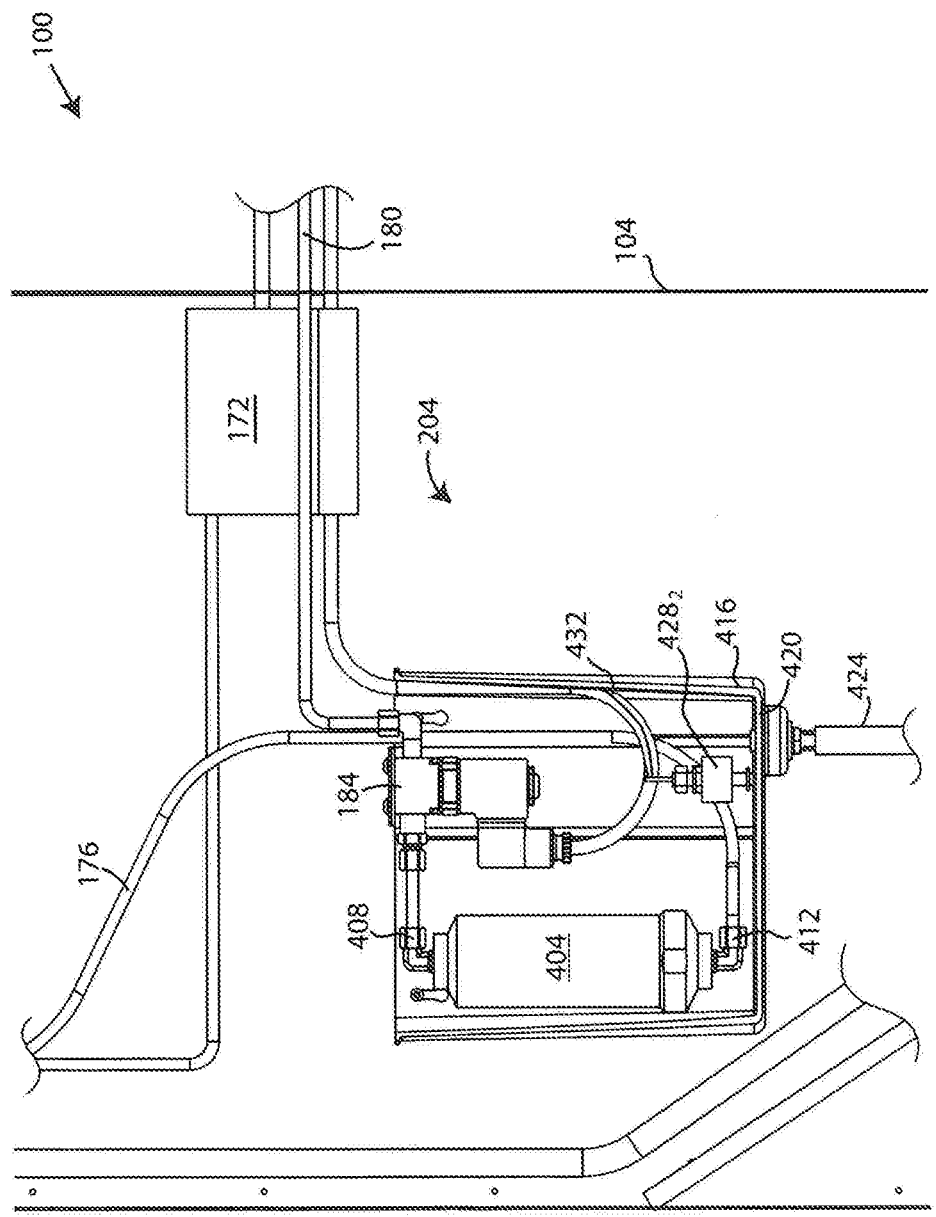
FIG. 19 is an enlarged view of region 19-19 in FIG. 5.
Figure 20:
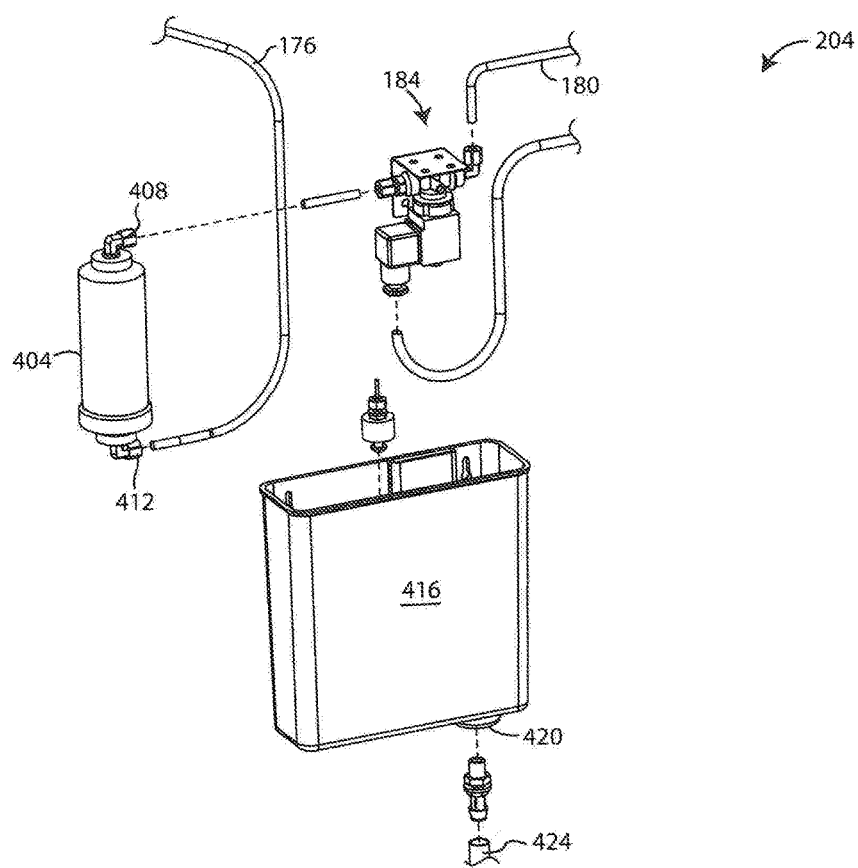
FIG. 20 is an exploded view of a filter portion of the humidification unit.

FIGS. 19 and 20 exemplify a filter portion 204 which may include a water filter 404 positioned in the water flow path between water supply 180 and misting portion 168. Water filter 404 may be any type of filter suitable for filtering water supplied to misting portion 168 (FIG. 5) for impurities, such as contaminants and minerals. For example, water filter 404 may include physical, chemical, or biological means of removing water impurities. Water filter 404 includes an inlet 408 downstream of water supply 180, and an outlet 412 upstream of misting portion 168 (FIG. 5). In the illustrated example, an optional shut-off valve 184 is positioned upstream of water filter inlet 408 between water filter inlet 408 and water supply 180. In alternative embodiments, shut-off valve 184 may be positioned downstream of water filter outlet 412 or may not be provided.

Figure 21:
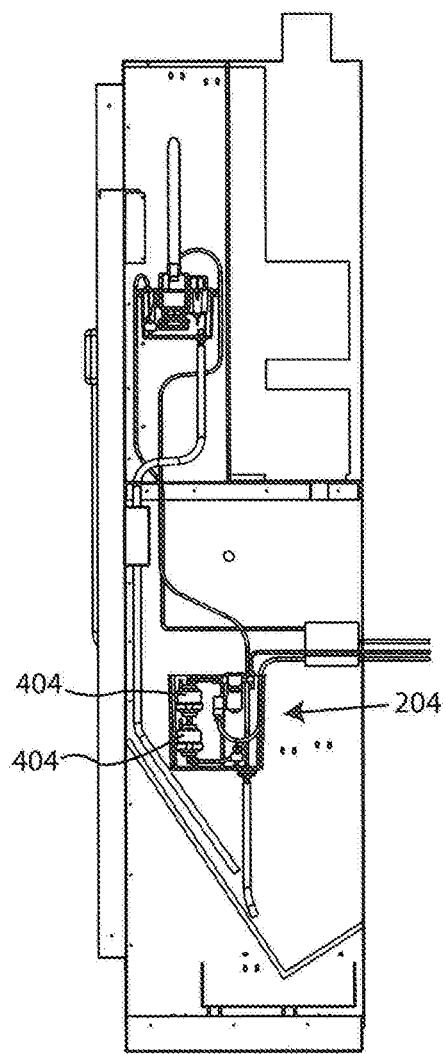
FIG. 21 is a cross-sectional view taken along line 5-5 in FIG. 1 in accordance with another embodiment.

Filter portion 204 may include any number of water filters 404. FIGS. 19 and 20 show an example of filter portion 204 including one water filter 404. An advantage of having a single water filter 404 is that only one water filter 404 needs to be periodically cleaned or replaced. FIG. 21 shows an example of filter portion 204 including a plurality of water filters 404 in series. An advantage of having a plurality of water filters in series 404 is that each water filter 404 may be specially configured to remove different impurities.

Referring again to FIGS. 19 and 20, in some embodiments, filter portion 204 may include a leak container 416 to collect water that may leak from water filter 404 and/or shut-off valve 184. As shown, water filter 404 and shut-off valve 184 may overlie at least a portion of an open interior of filter portion leak container 416 so that leaking water from filter portion 204 and/or shut-off valve 184 may fall by gravity into filter portion leak container 416. An advantage of this design is that filter portion leak container 416 may collect any water that may leak from water filter 404 and/or shut-off valve 184 instead of that water pooling inside fan coil housing 104 and potentially leaking into the apparatus surroundings (e.g. inside the wall in which apparatus 100 is recessed).

As shown, filter portion leak container 416 may include a drain 420 that provides an outlet for water collected in filter portion leak container 416. An advantage of this design is that water leaking from water filter 404 and/or shut-off valve 184 may be redirected through drain 420 to, e.g. a municipal drain, or recirculated back into the water flow path between water supply 180 and misting portion 168 (FIG. 5). In the illustrated example, a drain conduit 424 is connected to leak container drain 420 for directing drain water downstream.

Figure 22:
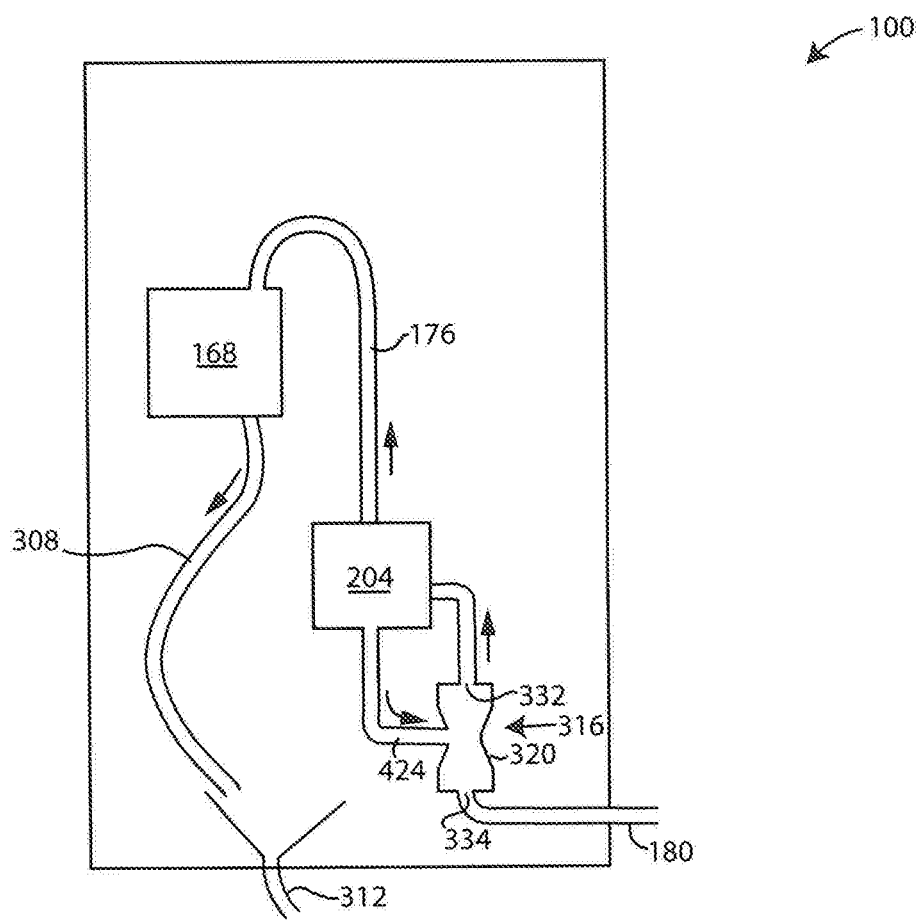
FIG. 22 is a schematic drawing of a fan coil apparatus in accordance with another embodiment.

FIG. 5 shows an example in which leak container drain conduit 424 directs drain water towards fan coil drain 312, which leads outside of fan coil apparatus 100, such as to a municipal drain or outdoors. FIG. 22 shows an example in which leak container drain conduit 424 directs water to recirculate back into water filter inlet 408. As shown, leak container drain conduit 424 may be fluidly connected to a venturi device 316. The venture device 316 combines the drain water with water from water supply 180 upstream of water filter 404. An advantage of this design is that water consumption is reduced by recycling the drain water instead of discarding the drain water (e.g. to a municipal drain).

Leak Detection Control System

The following is a description of leak detection control system that may be used by itself or in combination with one or more other features disclosed herein including one or more of an air scoop, a misting portion water impermeable container, mist distributor, a filter portion, an air permeable water retaining member and a treatment applicator.

In accordance with this feature, the water supply to, e. g, tank 224, may be shut off if a leak is detected. An advantage of this design is that water to the humidification unit may be stopped before, e. g., leak containers 296 or 416 overflow and spill water into the fan coil housing 104.

Figure 23:
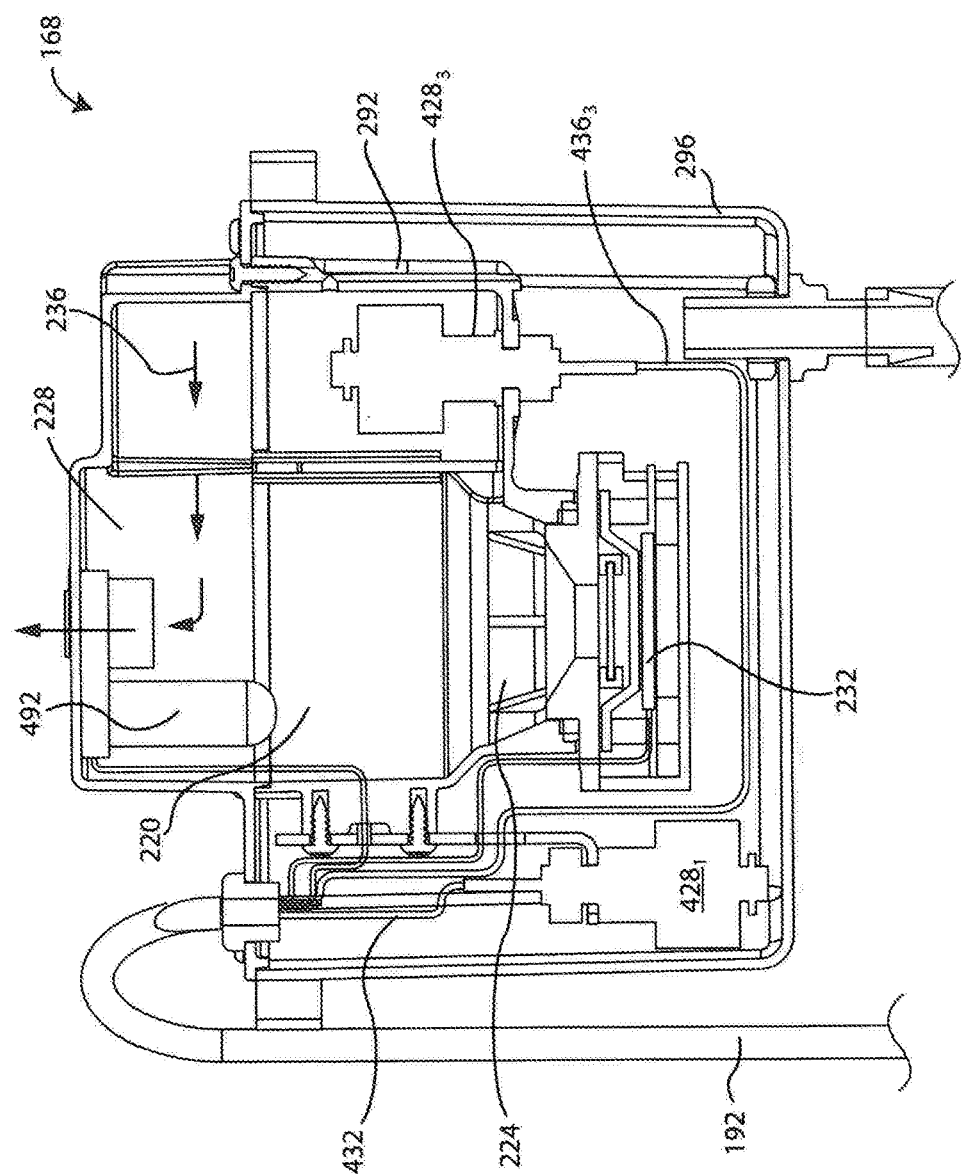
FIG. 23 is a cross-sectional view taken along line 23-23 in FIG. 8 with a leak water level detector sensing a lower water level.

As exemplified in FIGS. 19 and 23, one or both of misting portion 168 and filter portion 204 may include a leak water level detector 428. Leak water level detector 428 may be communicatively coupled (e.g. electrically connected) to a controller, which may be humidification unit controller 172. Humidification unit controller 172 may direct the shut-off valve 184 to move to the closed position in response to any one or more of the leak water level detectors 428 sensing a high water level. As exemplified, misting portion 168 may include a leak water level detector $428_1$ to sense a water level in misting portion leak container 296, or filter portion 204 may include a leak water level detector $428_2$ to sense a water level in filter portion leak container 416, or both.

Leak water level detectors 428 may have any configuration suitable for detecting a high water level condition in a leak container 296 or 416. For example, leak water level detectors 428 may include one or more float switches as exemplified, pressure sensors, optical sensors, capacitance sensors, ultrasonic sensors, or laser sensors. In the illustrated embodiment, water level detectors 428 are electrically connected to humidification unit controller 172 by wires 432, which may also provide water level detectors 428 with power to operate, if required. In other embodiments, other means of communication may be used including wireless (e.g., Bluetooth), optical, or the like.

Figure 24:
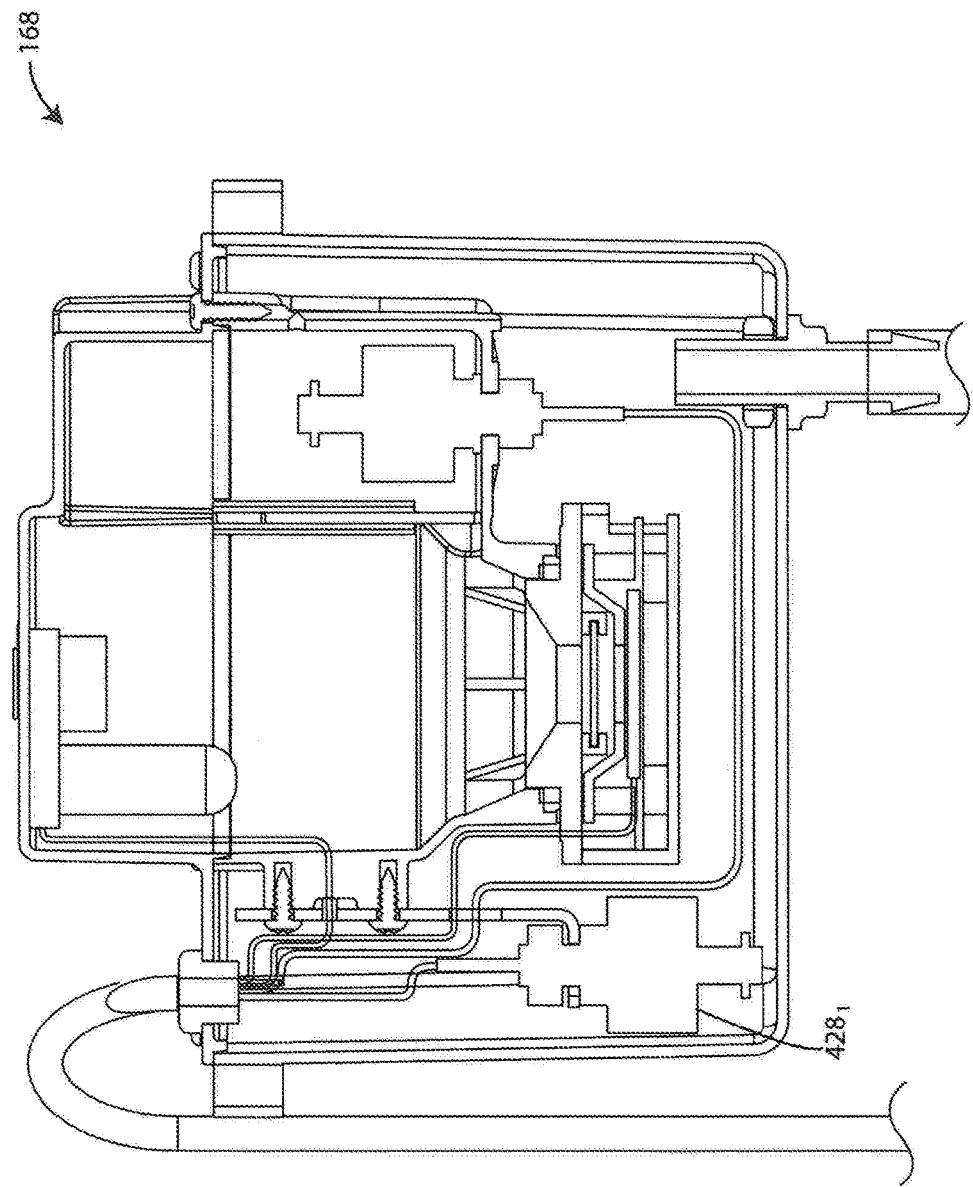
FIG. 24 is a cross-sectional view taken along line 23-23 in FIG. 8 with the leak water level detector sensing a high water level.

In some embodiments, leak water level detectors 428 may sense the presence of a high water level and a low water level in a leak container 296 or 416. FIG. 23 shows an example of leak water level detector 428 in a first position and sensing a low water level, and FIG. 24 shows an example of the leak water level detector $428_1$ in a second position and sensing a high water level.

Returning to FIGS. 19 and 23, preferably, humidification unit controller 172 directs shut-off valve 184 to move to its closed position in response to determining that any of the leak water level detectors 428 senses a high water level. For example, humidification unit controller 172 may intermittently poll leak water level detectors 428 for a water level status, leak water level detectors 428 may intermittently report the water level status to humidification unit controller 172, or humidification unit controller 172 may continuously monitor leak water level detectors 428 for a high or low water level status. Humidification unit controller 172 may permit shut-off valve 184 to move to its open position in response to determining that all of the leak water level detectors 428 sense a low water level. However, even if all of the leak water level detectors 428 sense a low water level, humidification unit controller 172 may yet direct shut-off valve 184 to move to or stay in the closed position until other factors are satisfied, such as receiving a signal from air regulating device 120 (FIG. 3) instructing that humidity is required.

In some embodiments, humidification unit controller 172 directs shut-off valve 184 to move to its closed position in response to determining that any one of the leak water level detectors 428 is not sensing a low water level, even if none of the leak water level detectors 428 is sensing a high water level. For example, humidification unit controller 172 may only direct or permit shut-off valve 184 to move to its open position in response to determining that each of the leak water level detectors 428 is sensing a lower water level.

Still referring to FIGS. 19 and 23, in some embodiments misting portion inner container 292 may include a water level detector $428_3$ to sense the water level in misting portion inner container 292 and/or water tank 224. Water level detector $428_3$ may be communicatively coupled (e.g. electrically connected) to humidification unit controller 172, such as by wire $436_3$. Humidification unit controller 172 may direct the shut-off valve 184 to move to the closed position in response to water level detector $428_3$ (or any other water level detector 428) sensing a high water level. An advantage of this design is that the water level in water tank 224 may be prevented from rising above a preset level, e.g., a the maximum water level that allows water mist production member 232 to generate water mist efficiently, and/or water tank 224 is prevented from overflowing. Once the inflow of water is shut off, the water level will lower again as the water mist production member 232 consumes water to generate water mist.

In some embodiments, water lever detector $428_3$ may also sense a low water level in water tank 224. In response, to water level detector $428_3$ detecting a low water level, humidification unit controller 172 (FIG. 5) may deactivate water mist production member 232. For example, humidification unit controller 172 (FIG. 5) may cut power to water mist production member 232 or signal water mist production member 232 to stop generating water mist. An advantage of this design is that water mist production member 232 may be prevented from damage by operating with insufficient water present. While water mist production member 232 is deactivated, the water level in water tank 224 may rise as water flows into misting portion 168. Once the water level in water tank 224 is at a safe operating water level (e.g. once water mist production member 232 ceases to sense a low water level), the water mist production member 232 may respond by re-activate water mist production member 232.

Figure 25:
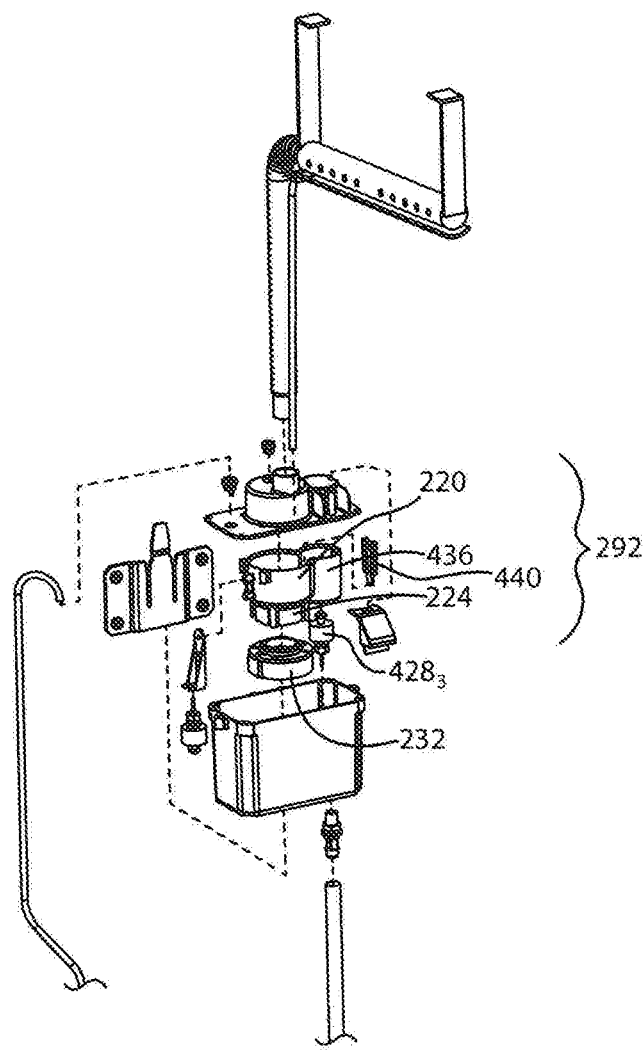
FIG. 25 is an exploded view of the misting portion.
Figure 26:
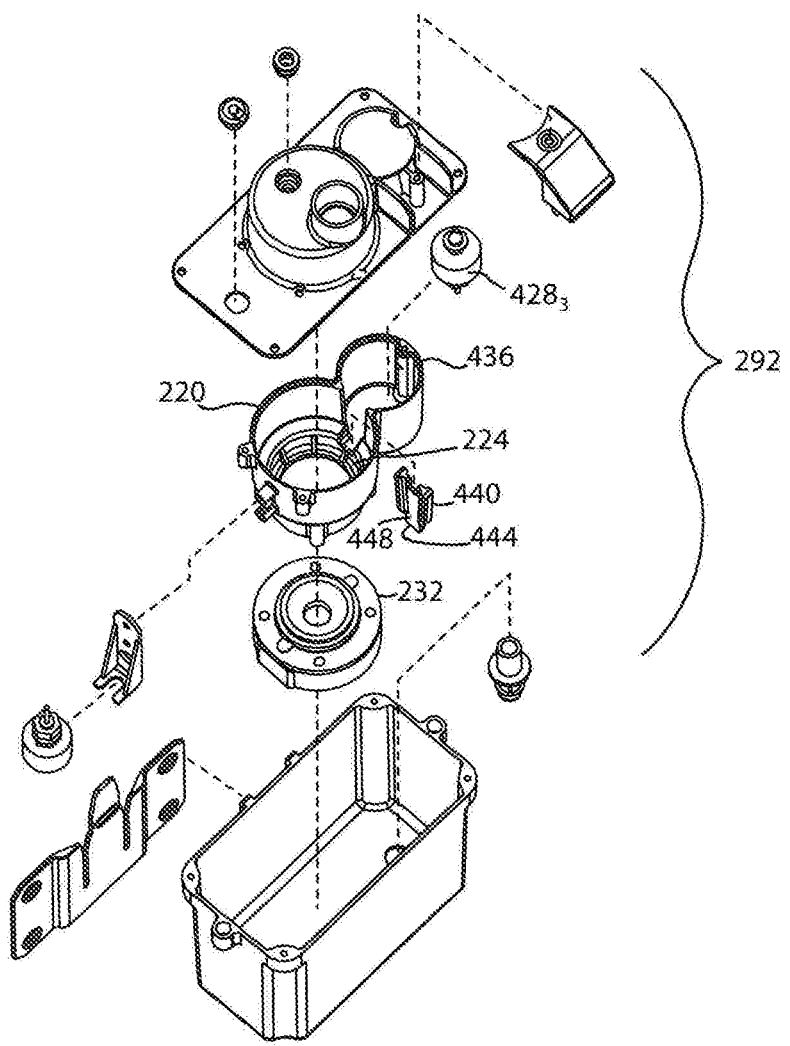
FIG. 26 is another exploded view of the misting portion.

Reference is now made to FIGS. 10 and 25-26. In some embodiments, water level detector $428_3$ may be positioned outside of the water tank 224. For example, misting portion inner container 292 may include a water mist production member chamber 220 including water tank 224, and a water reservoir 436. As exemplified, the water tank 224 and water reservoir 436 may be separated by a separating wall 440. An advantage of this design is that the water level detector $428_3$ is at least partially insulated from water mist production member 232. For example, separating wall 440 may at least partially insulate water level detector $428_3$ from the high frequency ultrasonic waves emitted by nebulizer 284, which may affect, interfere with, or damage water level detector $428_3$.

Misting portion water reservoir 436 is fluidly coupled with water tank 224 and may be laterally spaced therefrom so that the water level in water reservoir 436 may correspond to the water level in water tank 224. This allows water level detector $428_3$ to sense a high or low water level in water tank 224 based on the water level in misting portion water reservoir 436. In the illustrated example, misting portion water reservoir 436 is fluidly coupled to water tank 224 by a fluid flow port 444. Fluid flow port 444 may have any configuration that allows water to flow freely between water reservoir 436 and water tank 224. In the illustrated example, fluid flow port 444 is formed as an aperture, recess, or cutaway in a lower portion 448 of separating wall 440. Preferably, fluid flow port 444 is positioned at an elevation above water mist production member 232. It will be appreciated that by laterally positioning water reservoir 436 from tank 224, water level detector $428_3$ may be set such that the high water level in water reservoir 436 corresponds to a maximum desired water level in tank 224 and, similarly, the low water level in water reservoir 436 corresponds to a minimum desired water level in tank 224.

Optionally, the air flow path through the humidification unit may pass over water reservoir 436. Accordingly, as exemplified in FIG. 10, misting portion separating wall 440 may be configured to allow (e.g. not obstruct) misting portion air flow path 236 to pass over misting portion water reservoir 436 to the air plenum 228 above water tank 224. For example, misting portion separating wall 440 may have an upper end 452 spaced apart from misting portion upper wall 240 as shown, or may have one or more air flow ports to allow air to flow through.

Referring to FIGS. 5 and 10, humidification unit controller 172 may be any device suitable to execute the functionality described herein. For example, humidification unit 164 may be a computing device (e.g. including a processor and memory), or a logic circuit. In some embodiments, the relationship between the shut-off valve 184 and water level sensations by water level detectors 428 may be hardwired without use of humidification unit controller 172. For example, FIG. 32 shows an example power circuit 490 in which power to shut-off valve 184 depends on the position (or water level sensation) of water level detectors 428. In this example, shut-off valve 184 moves to the closed position upon losing power, and water level detectors 428 open the power circuit in response to detecting a high water level. As a result, shut-off valve 184 loses power and moves to the closed position in response to any of water level detectors 428 sensing a high water level.

As exemplified in FIG. 32, if water level sensor $428_1$ detects a high water level in misting portion leak container 296, (e.g., a float switch rises to a high water level position), then water level sensor $428_1$ may send a signal that opens circuit 490 as exemplified in FIG. 32. This may occur if, e.g., the drain of misting portion leak container 296 becomes blocked and the water level in misting portion leak container 296 rises and or there is a rapid leak and the water level in misting portion leak container 296 rises. In such a case, shut off valve 184 may move to the closed position (e.g., solenoid valve may be configured to move to the closed position when the circuit is open and no power is provided to the solenoid). It will be appreciated that when the water level drops in misting portion leak container 296, e.g., water is drained by the drain conduit, that the water level will drop and a signal may no longer be provided by the sensor (e.g., the float switch drops). Accordingly, the circuit will close, thereby providing power to shut-off valve 184 and causing the valve to open and permitting water to enter the apparatus.

Similarly, if water level sensor $428_3$ detects a high water level in misting portion inner container 292 and/or water tank 224 (e.g., a float switch rises to a high water level position), then water level sensor $428_3$ may send a signal that opens circuit 490 as exemplified in FIG. 32 and shut off valve 184 may move to the closed position. In such a case, the misting portion inner container 292 and/or water tank 224 will be at the high water level and no more water is required until the mist producing member has used sufficient water for the water level to drop and the sensor to no longer detect a high water level (e.g., a float switch drops from a high water level).

Similarly, if water level sensor $428_2$ detects a high water level in filter portion leak container 416 (e.g., a float switch rises to a high water level position), then water level sensor $428_2$ may send a signal that opens circuit 490 as exemplified in FIG. 32 and shut off valve 184 may move to the closed position. This may occur if, e.g., the drain of filter portion leak container 416 becomes blocked and the water level in filter portion leak container 416 rises and or there is a rapid leak and the water level in filter portion leak container 416 rises.

It will be appreciated that, as long as one high water level is detected, that shut off valve 184 will close the water inlet line.

In an alternate embodiment, circuit 490 may remain open until water level sensor $428_1$ detects a low water level in misting portion leak container 296, In a further alternate embodiment, shut-off valve may be configured to close if the circuit is closed. In such a case, water level sensors 428 may be configured to send a signal when not at a high water level. When they reach a high water level, they may cease sending a signal, in which case the circuit may close.

Treatment Applicator

The following is a description of a treatment applicator that may be used by itself or in combination with one or more other features disclosed herein including one or more of an air scoop, a misting portion water impermeable container, mist distributor, a filter portion, a leak detection control system and an air permeable water retaining member.

In accordance with this feature, a treatment applicator is provided which provides a disinfecting agent to the humidification unit to inhibit and, preferably prevent the growth of microorganisms, mold, bacteria, and the like (collectively referred herein as 'organisms').

As exemplified in FIG. 27, fan coil air flow path 136 may comprise a humidification section 480 in which water mist discharged by mist distributor 340 mixes with air flow in the fan coil air flow path 136. In the illustrated embodiment, the humidification section 480 is shown between heating zone 148 and fan coil air outlet 116, such as in air exit plenum 156. However, in other embodiments, humidification section 480 may be positioned elsewhere along the fan coil air flow path 136.

The conditions in humidification section 480 (e.g. presence of hot and humid air, and possibly accumulated water droplets) may result in the growth of organisms. Such organisms may have a negative effect of the air purity discharged from fan coil apparatus 100. In some embodiments, fan coil apparatus 100 includes one or more treatment applicators 484 that provide one or more disinfecting agents in the humidification section 480 to reduce or eliminate organisms in the humidification section 480. An advantage of this design is that it helps to purify the air discharged from fan coil apparatus 100 by reducing or eliminating potentially harmful organisms that may be come entrained in the air flow.

Disinfecting agents may be any element or emission that may reduce or inhibit growth of organisms in humidification section 480, or that are harmful or lethal to organisms that may grow in humidification section 480. Examples include ultra-violet (UV) light, ozone ($O_3$), and hydrogen peroxide ($H_2O_2$). In the illustrated embodiment, fan coil apparatus 100 is shown including a UV light emitter $484_1$, an ozone gas emitter $484_2$, and a hydrogen peroxide vapor emitter $484_3$, which emit UV light, ozone gas, and hydrogen peroxide vapor, respectively, into humidification section 480.

Ozone gas may be highly effective for purifying an air flow. However, ozone gas may be also harmful to breath for humans and animals. Some embodiments which include an ozone gas emitter $484_2$ may also include an ozone destructor material 488 positioned in the fan coil air flow path 136 downstream of ozone gas emitter $484_2$. The ozone destructor material 488 may be any material that can remove ozone gas from the air flow by adsorption or conversion to one or more other molecules. Examples include activated carbon or an ozone catalyst that converts ozone ($O_3$) to oxygen ($O_2$). An advantage of this design is that the ozone gas that is added to the air flow to counteract organisms in the humidification section 480 may be removed before the air flow is discharged from fan coil apparatus 100. This can allow a fan coil apparatus 100 including ozone gas emitter 484$_2$ to be safely employed in, e.g. residential spaces.

Alternately or in addition, as exemplified in FIG. 23, misting portion 168 may comprise a treatment applicator 492 to counteract organisms inside misting portion 168. For example, misting portion 168 may include a treatment applicator 492 that provides a disinfecting agent in misting portion inner container 292. An advantage of this design is that it can mitigate or eliminate the growth of organisms inside misting portion inner container 292, such as organisms that may grow in water tank 224, air plenum 228, or along misting portion air flow path 236. Treatment applicator 492 may be the same as or similar to treatment applicator 484. As with treatment applicator 484, treatment applicator 492 may produce any disinfecting agent that may reduce or inhibit growth of organisms in misting portion 168, or that may be harmful or lethal to organisms that may grow in misting portion 168. Examples of disinfecting agents include ultra-violet (UV) light, ozone ($O_3$), and hydrogen peroxide ($H_2O_2$). In the illustrated embodiment, misting portion 168 is shown including a UV light emitter 492, which emits UV light into water mist production chamber 220.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A fan coil apparatus comprising:
   (a) an air flow path extending from a heating zone to a fan coil air outlet and including a humidification section;
   (b) a humidification unit comprising a humidification unit water droplet outlet and an air permeable water retaining member, wherein the air permeable water retaining member and the humidification unit water droplet outlet are provided in the humidification section and the air permeable water retaining member is positioned downstream from the humidification unit water droplet outlet;
   (c) a water filter upstream of the humidification unit; and,
   (d) a treatment applicator providing a disinfecting agent directly upstream from the air permeable water retaining member.

2. The fan coil of claim 1 wherein the disinfecting agent comprises one or more of ozone, UV light and hydrogen peroxide.

3. The fan coil of claim 2 wherein the disinfecting agent comprises ozone and the fan coil further comprises an ozone destructor material positioned upstream from an air outlet of the fan coil.

4. The fan coil of claim 1 wherein the humidification unit is located in an air exit plenum of the fan coil.

5. The fan coil of claim 4 wherein the disinfecting agent is provided in the air exit plenum.

6. The fan coil of claim 5 wherein the disinfecting agent comprises one or more of ozone and hydrogen peroxide and the disinfecting agent is introduced into the air exit plenum.

7. The fan coil of claim 6 wherein the disinfecting agent comprises ozone and the fan coil further comprises an ozone destructor material positioned downstream from the air permeable water retaining member.

8. The fan coil of claim 5 wherein the disinfecting agent comprises a UV light source and the UV light source is located in the air exit plenum.

9. The humidification unit of claim 5 wherein the disinfecting agent comprises one or more of ozone and hydrogen peroxide and the disinfecting agent is introduced into the humidification unit upstream from the air permeable water retaining member.

10. A humidification unit for a fan coil apparatus, the humidification unit comprising:
    (a) a humidification unit water droplet outlet;
    (b) an air permeable water retaining member positioned downstream from the humidification unit water droplet outlet; and,
    (c) a treatment applicator providing a disinfecting agent upstream from the air permeable water retaining member
    wherein the disinfecting agent comprises ozone and the humidification unit further comprises an ozone destructor material positioned upstream from an air outlet of the fan coil.

11. The humidification unit of claim 10 wherein the disinfecting agent comprises ozone and the humidification unit further comprises an ozone destructor material positioned downstream from the air permeable water retaining member.

12. The humidification unit of claim 10 wherein the disinfecting agent comprises a UV light source and the UV light source is located between the humidification unit water droplet outlet and the air permeable water retaining member.

* * * * *